US010696980B2

(12) United States Patent
Schultheiss

(10) Patent No.: US 10,696,980 B2
(45) **Date of Patent: *Jun. 30, 2020**

(54) METHOD OF INCREASING RESISTANCE AGAINST SOYBEAN RUST IN TRANSGENIC PLANTS BY ADR-1-GENE

(71) Applicant: BASF PLANT SCIENCE COMPANY GMBH, Ludwigshafen (DE)

(72) Inventor: Holger Schultheiss, Boehl-Iggelheim (DE)

(73) Assignee: BASF Plant Science Company GmbH, Ludwigshafen (DE)

( * ) Notice: Subject to any disclaimer, the term of this patent is extended or adjusted under 35 U.S.C. 154(b) by 155 days.

This patent is subject to a terminal disclaimer.

(21) Appl. No.: 15/681,684

(22) Filed: Aug. 21, 2017

(65) Prior Publication Data

US 2018/0044695 A1 Feb. 15, 2018

Related U.S. Application Data

(63) Continuation of application No. 13/817,512, filed as application No. PCT/IB2011/053615 on Aug. 16, 2011, now Pat. No. 9,856,493.

(60) Provisional application No. 61/375,053, filed on Aug. 19, 2010.

(30) Foreign Application Priority Data

Aug. 19, 2010 (EP) .................................... 10173393

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
None
See application file for complete search history.

(56) References Cited

U.S. PATENT DOCUMENTS

| | | | | |
|---|---|---|---|---|
| 4,992,375 | A | 2/1991 | Wright | |
| 5,416,011 | A | 5/1995 | Hinchee et al. | |
| 5,569,834 | A | 10/1996 | Hinchee et al. | |
| 5,824,877 | A | 10/1998 | Hinchee et al. | |
| 6,384,301 | B1 | 5/2002 | Martinell et al. | |
| 7,273,965 | B2 | 9/2007 | Ali et al. | |
| 2007/0192905 | A1* | 8/2007 | Piller ................. | A61K 39/0005 800/288 |
| 2010/0088777 | A1 | 4/2010 | Schultheiss et al. | |
| 2011/0252501 | A1* | 10/2011 | Abad ................. | C12N 15/8261 800/275 |
| 2013/0185824 | A1 | 7/2013 | Schultheiss et al. | |

FOREIGN PATENT DOCUMENTS

| | | | | |
|---|---|---|---|---|
| EP | 0301749 A2 | 2/1989 | | |
| WO | WO-02/20791 A1 | 3/2002 | | |
| WO | WO-0220791 A1 * | 3/2002 | ............. | A01N 65/00 |
| WO | WO-2008/017706 A1 | 2/2008 | | |
| WO | WO-2008/049865 A2 | 5/2008 | | |
| WO | WO-2010/009404 A2 | 1/2010 | | |

OTHER PUBLICATIONS

Bonardi et al (Expanded functions for a family of plant intracellular immune receptors beyond specific recognition of pathogen effectors. PNAS. 108:16463-16468, 2011) (Year: 2011).*

Fourgoux-Nicol et al (1999, Plant Molecular Biology 40: 857-872) (Year: 1999).*

Grant et al (Targeted Activation Tagging of the *Arabidopsis* NBS-LRR gene, ADR1, Conveys Resistance to Virulent Pathogens. MPMI vol. 16, No. 8, pp. 669-680, 2003). (Year: 2003).*

Gryson et al (Detection of DNA During the Refining of Soybean Oil. JAOCS, vol. 79, No. 2, 171-174, 2002) (Year: 2002).*

Schmitthenner (Phytophthora Rot of Soybean. PMN. 1-6, 2000) (Year: 2000).*

*Arabidopsis thaliana* add Gene for CC-NBS-LRR Disease Resistance Protein, NCB' Database, GenBank Accession No. AJ581996, Sep. 9, 2003.

RecName; Full=Disease Resistance Protein ADR1; AltName: Full= Activated Disease Resistance Protein 1, NCBI Database, GenBank Accession No. Q9FW44, Apr. 26, 2005.

Choi et al., Expression Patterns in Soybean Resistant to *Phakopsora pachyrhizi* Reveal the Importance of Peroxidases and Lipoxygenases, Funct. Integr. Genomics, 2008, vol. 8, pp. 341-359.

Fourgoux-Nicol et al., Isolation of rapeseed genes expressed early and specifically during development of the male gametophyte, Plant Molecular Biology, 40: 857-872 (1999).

Frederick et al., Polymerase Chain Reaction Assays for the Detection and Discrimination of the Soybean Rust Pathogens *Phakopsora pachyrhizi* and *P. meibomiae*, Phytopathology, 2002, vol. 92, No. 2, pp. 217-227.

Friedberg, Automated protein function prediction—the genomic challenge, Brief Bioinformatics, 7: 225-242 (2006).

Grant et al., Targeted Activation Tagging of the *Arabidopsis NBS-LRR* Gene, *ADR1*, Conveys Resistance to Virulent Pathogens, Mol, Plant Microbe Interact., 16(8):669-80 (2003).

Guo et al., Protein tolerance to random amino acid change, Proc. Natl. Acad. Sci. USA 101:9205-10 (2004).

Hill et al., Functional analysis of conserved histidines in ADP-glucose pyrophosphorylase from *Escherichia coli*., Biochem. Biophys. Res. Comm., 244:573-7 (1998).

(Continued)

*Primary Examiner* — Medina A Ibrahim
*Assistant Examiner* — Wayne Zhong
(74) *Attorney, Agent, or Firm* — Marshall, Gerstein & Borun LLP

(57) ABSTRACT

The present invention relates to a method of increasing resistance against soybean rust in transgenic plants and/or plant cells. In these plants, the content and/or the activity of an ADR-1-protein are increased in comparison to the wild-type plants not including a recombinant ADR-1-gene.

5 Claims, 9 Drawing Sheets

Specification includes a Sequence Listing.

(56) References Cited

OTHER PUBLICATIONS

Hoefle et al., Transgenic Suppression of Cell Death Limits Penetration Success of the Soybean Rust Fungus *Phakopsora pachyrhizi* into Epidermal Cells of Barley, Phytopathology, 2009, vol. 99, No. 3, pp. 220-226.
International Search Report for PCT/162011/053615 dated Jan. 5, 2012.
Oktem et al Revealing Response of Plants to Biotic and Abiotic Stresses with Microarray Technology, Genes, Genomes and Genomics, 2008, vol. 2, No. 1, pp. 14-48.
Oloka et al., Potential for Soybean Rust Tolerance among Elite Soybean Lines in Uganda, Crop Protection, 2009, vol. 28, pp. 1076-1080.
Rytter et al., Additional Alternative Hosts of *Phakopsora pachyrhizi*, Causal Agent of Soybean Rust, Plant Disease, 1984, vol. 68, No. 9, pp. 618-819.
Sinclair et al., eds., Proceedings of the Soybean Rust Workshop, 1996. Soybean Rust Workshop, Aug. 9-11, 1995. College of Agricultural, Consumer, and Environmental Sciences, National Soybean Research Laboratory Publication No. 1, Urbana, Illinois.
Soria-Guerra et al., Transcriptome Analysis of Resistant and Susceptible Genotypes of *Glycine tomentella* during *Phakopsora pachyrhizi* Infection Reveals Novel Rust Resistance Genes, Theor. Appl. Genet., 2010, vol. 120, pp. 1315-1333.
Chini and Loake, “Motifs specific for the ADR1 NBS-LRR protein family in *Arabidopsis* are conserved among NBS-LRR sequences from both dicotyledonous and monocotyledonous plants,” Planta, Jun. 2005;221(4):597-601. Epub May 12, 2005.

* cited by examiner

Figure 1 (SEQ -ID-No. 1)

atggcttcgttcatagatcttttcgccggcgacatcacgacgcaactcttaaagctgctcgctctagtagctaacacagtctacagttg
caaaggaatcgccgaacgactgatcacgatgatcagagacgttcaaccaacgatcagggagatccaatacagtggcgcgga
gctgagtaaccatcaccaaactcaactgggagtattctatgagatcttggagaaagcaagaaagctatgtgaaaaggttttaaga
tgcaataggtggaaccttaaacatgtgtaccacgcgaataagatgaaggatctcgagaaacaaatatctcgtttcctcaacagcc
agattttgctctttgttcttgctgaggtatgtcatctacgggtcaatggtgacaggattgagaggaatatggatagactgttgactgagc
ggaatgattctttgtcgtttccggagactatgatggagattgagacggtaagcgatccggagattcagacggtattggaattgggga
agaaaaaggtgaaggagatgatgtttaagtttacggatacacatttgtttgggatctctggaatgagcggttcagggaaaaccact
cttgcaatagagctttcaaaggacgatgatgttcgaggactctttaagaataaggttttgtttttgactgtgtcacggtctccgaattttga
gaatttggagtcttgtatacgagaatttctttatgatggagttcatcaacggaagctagtgattcttgatgatgtttggacaagggagtc
cttggacaggctgatgtctaaaattcgtggaagcactactttagtagtgtcacggtccaagcttgcagatcctagaaccacctacaa
tgtggaattattaaagaaagatgaagcaatgtctcttttgtgtctctgtgctttcgaacaaaagtccccgccttctccattcaacaaatat
ttggtgaagcaggttgttgatgagtgtaaaggtttacctttatctttgaaagttcttggtgcttcgttaaaaaacaaacctgaaagatatt
gggaaggcgtagtgaagaggttattaagaggagaagctgctgatgaaactcatgagagcagagtgtttgctcatatggaagaa
agtctagaaaacctcgacccgaaaatccgagactgtttcttggatatgggtgctttccctgaagacaagaagatccctcttgatcttc
tcacgagcgtgtgggttgagaggcatgatattgacgaggaaactgcgttttcctttgttcttcgtttagctgacaagaatctccttactat
agtgaacaatccgaggtttggcgatgtgcacattggctactatgatgtatttgtgacgcaacacgatgttttgagagacctagccctt
catatgtccaatcgtgtggacgtaaataggagagagcggttattaatgccaaaaacagagccagtgcttccaagagaatgggaa
aagaataaagatgagccatttgatgccaagatagtttcccttcatacaggggaaatggatgaaatgaattggtttgacatggacct
ccctaaggcagaagttttaatactgaacttctcttcggacaactacgtcttgccaccatttattggtaagatgagtagactcagggtgc
tcgtgattatcaacaatggcatgtctcctgcgcgtctacatggcttctccatctttgccaatttggccaaactgaggagtctctggctca
agagggtacatgtccctgaactcaccagctgcaccattccactgaaaaacctgcacaagatacatctaatcttttgtaaggtcaag
aacagctttgttcagacgtcattcgacatctcgaaaatattcccaagcttgtctgatctcactattgatcactgtgatgatcttttggaact
aaaatccatatttggaataacctctctcaactctctcagcataaccaactgtccacggattcttgaattgcccaagaatttgagtaac
gtacagtcccttgaacgtctaaggttatatgcctgccccgagctgatatccctcccggtcgaagtttgtgagctgccatgtctaaagta
cgttgacatttcacagtgtgtcagcctggtttctcttcctgaaaagtttggaaagctagggagtcttgagaaaattgacatgagagaat
gcagtttattgggtttaccaagttctgtagctgcacttgtgtctctacgccatgtcatttgcgatgaggagacttcgtctatgtgggaaat
ggtcaagaaggtggttcctgaactttgcattgaagtcgccaaaaaatgcttcaccgtggattggcttgacgattag Figure 2 (SEQ-ID-NO. 2)

MASFIDLFAGDITTQLLKLLALVANTVYSCKGIAERLITMIRDVQPTIREIQYSGAELSNHHQTQ
LGVFYEILEKARKLCEKVLRCNRWNLKHVYHANKMKDLEKQISRFLNSQILLFVLAEVCHLRV
NGDRIERNMDRLLTERNDSLSFPETMMEIETVSDPEIQTVLELGKKKVKEMMFKFTDTHLFGI
SGMSGSGKTTLAIELSKDDDVRGLFKNKVLFLTVSRSPNFENLESCIREFLYDGVHQRKLVIL
DDVWTRESLDRLMSKIRGSTTLVVSRSKLADPRTTYNVELLKKDEAMSLLCLCAFEQKSPPS
PFNKYLVKQVVDECKGLPLSLKVLGASLKNKPERYWEGVVKRLLRGEAADETHESRVFAHM
EESLENLDPKIRDCFLDMGAFPEDKKIPLDLLTSVWVERHDIDEETAFSFVLRLADKNLLTIVN
NPRFGDVHIGYYDVFVTQHDVLRDLALHMSNRVDVNRRERLLMPKTEPVLPREWEKNKDE
PFDAKIVSLHTGEMDEMNWFDMDLPKAEVLILNFSSDNYVLPPFIGKMSRLRVLVIINNGMSP
ARLHGFSIFANLAKLRSLWLKRVHVPELTSCTIPLKNLHKIHLIFCKVKNSFVQTSFDISKIFPS
LSDLTIDHCDDLLELKSIFGITSLNSLSITNCPRILELPKNLSNVQSLERLRLYACPELISLPVEV
CELPCLKYVDISQCVSLVSLPEKFGKLGSLEKIDMRECSLLGLPSSVAALVSLRHVICDEETS
SMWEMVKKVVPELCIEVAKKCFTVDWLDD*

Figure 3

Coiled-coil domain

DNA Pos 286 - 336bp:
Cacgcgaataagatgaaggatctcgagaaacaaatatctcgtttcctcaac (SEQ-ID-No. 3)

Protein: H96-N112:
HANKMKDLEKQISRFLN (SEQ-ID-No. 4)

NBS-Domain:

DNA Pos 562-1386
Ttgtttgggatctctggaatgagcggttcagggaaaaccactcttgcaatagagctttcaaaggacgatgatgttcgaggactcttta
agaataaggttttgtttttgactgtgtcacggtctccgaattttgagaatttggagtcttgtatacgagaatttctttatgatggagttcatca
acggaagctagtgattcttgatgatgtttggacaagggagtccttggacaggctgatgtctaaaattcgtggaagcactactttagta
gtgtcacggtccaagcttgcagatcctagaaccacctacaatgtggaattattaaagaaagatgaagcaatgtctcttttgtgtctct
gtgctttcgaacaaaagtccccgccttctccattcaacaaatatttggtgaagcaggttgttgatgagtgtaaaggtttacctttatcttt
gaaagttcttggtgcttcgttaaaaaacaaacctgaaagatattgggaaggcgtagtgaagaggttattaagaggagaagctgct
gatgaaactcatgagagcagagtgtttgctcatatggaagaaagtctagaaaacctcgacccgaaaatccgagactgtttcttgg
atatgggtgctttccctgaagacaagaagatccctcttgatcttctcacgagcgtgtgggttgagaggcatgatattgacgaggaaa
ctgcgttttcctttgttcttcgtttagctgacaagaatctccttactatagtgaacaatccgaggtttggcgatgtgcacattggctactatg
atgtatttgtgacgcaacacgatgtt (SEQ-ID-No. 5)

Protein: L188-V462:
LFGISGMSGSGKTTLAIELSKDDDVRGLFKNKVLFLTVSRSPNFENLESCIREFLYDGVHQRK
LVILDDVWTRESLDRLMSKIRGSTTLVVSRSKLADPRTTYNVELLKKDEAMSLLCLCAFEQKS
PPSPFNKYLVKQVVDECKGLPLSLKVLGASLKNKPERYWEGVVKRLLRGEAADETHESRVF
AHMEESLENLDPKIRDCFLDMGAFPEDKKIPLDLLTSVWVERHDIDEETAFSFVLRLADKNLL
TIVNNPRFGDVHIGYYDVFVTQHDV (SEQ-ID-No. 6)

LRR domain

DNA Pos: 1387-2208
Ttgagagacctagcccttcatatgtccaatcgtgtggacgtaaataggagagagcggttattaatgccaaaaacagagccagtg
cttccaagagaatgggaaaagaataaagatgagccatttgatgccaagatagtttcccttcatacaggggaaatggatgaaatg
aattggtttgacatggacctccctaaggcagaagttttaatactgaacttctcttcggacaactacgtcttgccaccatttattggtaag
atgagtagactcagggtgctcgtgattatcaacaatggcatgtctcctgcgcgtctacatggcttctccatctttgccaatttggccaa
actgaggagtctctggctcaagagggtacatgtccctgaactcaccagctgcaccattccactgaaaaacctgcacaagatacat
ctaatcttttgtaaggtcaagaacagctttgttcagacgtcattcgacatctcgaaaatattcccaagcttgtctgatctcactattgatc
actgtgatgatcttttggaactaaaatccatatttggaataacctctctcaactctctcagcataaccaactgtccacggattcttgaatt
gcccaagaatttgagtaacgtacagtcccttgaacgtctaaggttatatgcctgccccgagctgatatccctcccggtcgaagtttgt
gagctgccatgtctaaagtacgttgacatttcacagtgtgtcagcctggtttctcttcctgaaaagtttggaaagctagggagtcttga
gaaaattgacatgagagaatgcagtttattg (SEQ-ID-No. 7)

Protein: L463-L736:
LRDLALHMSNRVDVNRRERLLMPKTEPVLPREWEKNKDEPFDAKIVSLHTGEMDEMNWFD
MDLPKAEVLILNFSSDNYVLPPFIGKMSRLRVLVIINNGMSPARLHGFSIFANLAKLRSLWLKR
VHVPELTSCTIPLKNLHKIHLIFCKVKNSFVQTSFDISKIFPSLSDLTIDHCDDLLELKSIFGITSL
NSLSITNCPRILELPKNLSNVQSLERLRLYACPELISLPVEVCELPCLKYVDISQCVSLVSLPE
KFGKLGSLEKIDMRECSLL (SEQ-ID-No. 8)

Figure 5 (SEQ-ID-No. 9)

gtgattttgtgccgagctgccggtcggggagctgttggctggctggtggcaggatatattgtggtgtaaacaaattgacgcttagacaacttaataa
cacattgcggacgtctttaatgtactgaattaacatccgtttgatacttgtctaaaattggctgatttcgagtgcatctatgcataaaaacaatctaatg
acaattattaccaagcagagcttgacaggaggcccgatctagtaacatagatgacaccgcgcgcgataatttatcctagtttgcgcgctatatttt
gttttctatcgcgtattaaatgtataattgcgggactctaatcataaaaacccatctcataaataacgtcatgcattacatgttaattattacatgcttaa
cgtaattcaacagaaattatatgataatcatcgcaagaccggcaacaggattcaatcttaagaaactttattgccaaatgtttgaacgatcgggg
atcatccgggtctgtggcgggaactccacgaaaatatccgaacgcagcaagatctagagcttgggtcgggaaattaccctgttatccctatcag
tatttaatccggccatctccttccgttatgacatcgttgaaagtgccaccattcgggatcatcggcaacacatgttcttggtgcggacaaatcacatc
caacaggtaaggtcctggtgtatccagcattgtctgaatagcttctcggagatctgctttctttgtcaccctcgccgctggaatcccgcaagctgctg
caaacagcaacatgttcgggaatatctcgtcctcctgagccggatccccgagaaatgtgtgagctcggttagctttgtagaaccgatcttcccatt
gcataaccatgccaagatgctggttgtttaataaaagtaccttcactggaagattctctacacgaatagtggctagctcttgcacattcattataaag
cttccatctccgtcaatatccacaactatcgcatcagggttagcaacagacgctccaatcgcagcaggaagtccaaatcccatagctccaagg
cctcctgatgatagccactgccttggtttcttgtaattgtagaactgcgccgcccacatttgatgttgcccgacaccagtacttattatggcttttccatc
agtcaactcatcaaggaccttaatcgcatactgtggaggaatagcttccccaaacgtcttaaagctcaacggaaacttctgtttctgtacgttcaac
tcattcctccaaactccaaaatcaagcttaagctcctccgctcggttctcaagaaccttattcatcccttgcaaagccagcttaacatcaccacaca
cagacacatgaggagtcttattcttcccaatctcagccgagtcaatatcaatatgaacaatcttagccctactagcaaaagcctcaagcttaccc
gtgacacgatcatcaaaccttaccccaaacgccaacaacaaatcactatgctccacagcgtaatttgcatacacagtcccatgcattccaagc
atatgtaacgacaactcatcatcacaaggataagatcccagccccatcaacgtactcgcaacagggatccccgtaagctcaacaaacctacc
caattcatcgctagaattcaaacaaccaccaccaacatacaacacaggcttcttagactcagaaatcaacctaacaatctgctccaaatgaga
atcttccggaggtttaggcatcctagacatataaccaggtaatctcatagcctgttcccaattaggaatcgcaagctgttgttgaatatctttaggaa
catcaaccaaaacaggtccaggtctaccagaagtagctaaaaagaaagcttcctcaataatcctagggatatcttcaacatccatcacaagat
agttatgcttcgtaatcgaacgcgttacctcaacaatcggagtctcttgaaacgcatctgtaccaatcatacgacgagggacttgtcctgtgattgc
tacaagaggaacactatctaacaacgcatcggctaatccgctaacgagatttgtagctccgggacctgaagtggctatacagatacctggttta
cctgaggatcgagcgtatccttctgctgcgaatacacctccttgttcgtgacgaggaaggacgttacggattgaggaagagcgggttaaggcttg
gtgaatctccattgatgtacctccagggtaagcgaatacggtttctacgccttgacgttctaaagcttcgacgaggatatcagcgcctttgcggggt
tgatctggagcgaatcgggagatgaatgtttcgggtttggtaggtttggttggagagggagtggttgtgacattggtggttgtgttgagcacggcgg
agatggaggagggagagctggatttgataccgcggcggcgggaggaggaggatgatttgttggggtttagggagaatgggagggagaatct
ggagattggtaatggtgatttggaggaggaaggagatggtttggtggagaaggagatcgaagaagatgttgttgttgttgttgttgccgccgccat
ggttcagctgcacatacataacatatcaagatcagaacacacatatacacacacaaatacaatcaagtcaacaactccaaaaagtccagatc
tacatatatacatacgtaaataacaaaatcatgtaaataatcacaatcatgtaatccagatctatgcacatatatatatacacaattaataaaaaa
aatgatataacagatctatatctatgtatgtaacaacacaatcagatgagagaagtgatgttttcagatctgtatacatacaaacacaaacagat
gaacaattgatacgtagatccatatgtatacgtacaattagctacacgattaaatgaaaaaaatcaacgatttcggattggtacacacaaacgc
aacaatatgaagaaattcatatctgattagatataaacataaccacgtgtagatacacagtcaaatcaacaaatttatagcttctaaacggatga
gatgaacaagataaagatattcacataaggcatacataagataagcagattaacaaactagcaataatacatacctaattaaaacaaggaat
aacagagagagagagagagagagagatttaccttgaaaatgaagaggagaagagaggatttcttaaaattggggtagagaaagaaag
atgatgaattgtgagaaaggagagatagaagggggggttgtatatataggctgtagaagattatttttgtgtttgaggcggtgaaggaagaggg
gatctgactatgacacgtttgcggttacgtatttcgataggagtctttcaacgcttaacgccgttactctatatgaccgtttgggccgtaacggggcc
gtttgttaacgctgatgttgattcttttctttctttctttcttcctttttttaaagaagcaattgtacaatcgttgctagctgtcaaacggataattcggatacgg
atatgcctatattcatatccgtaatttttggattcgaattttcccctctagggataacagggtaatgcccgatctagtaacatagatgacaccgcgcg
cgataatttatcctagtttgcgcgctatattttgttttctatcgcgtattaaatgtataattgcgggactctaatcataaaaacccatctcataaataacgt
catgcattacatgttaattattacatgcttaacgtaattcaacagaaattatatgataatcatcgcaagaccggcaacaggattcaatcttaagaaa
ctttattgccaaatgtttgaacgatggtacctcgagcggccgccagtgtgatggatatctgcagaattcgcccttaaaaaagatatccggccagtg
aattatcaactatgtataataaagttgggtacccccgatcccccccactccgccctacactcgtatatatatgcctaaacctgccccgttcctcatat
gtgatattattatttcattattaggtataagatagtaaacgataaggaaagacaatttattgag
aaagccatgctaaaatatagatagatataccttagcaggtgtttattttacaacataacataacatagtagctagccagcaggcaggctaaaac
atagtatagtctatctgcaggggggtacggtcgaggcggccttaattaatcgataggggaagcttggcgtaatcatggccactttgtacaagaaa
gctgggtccatgattacgccaagcttgcatgcccatatgctcgaggcggccgcggcgcgccaattgactagtaggcctatcgattaattaaggc
cgcagatatcagatctggtcgacctaatcgtcaagccaatccacggtgaagcatttttggcgacttcaatgcaaagttcaggaaccaccttcttg
accatttcccacatagacgaagtctcctcatcgcaaatgacatggcgtagagacacaagtgcagctacagaacttggtaaacccaataaactg
cattctctcatgtcaattttctcaagactccctagctttccaaacttttcaggaagagaaaccaggctgacacactgtgaaatgtcaacgtactttag
acatggcagctcacaaacttcgaccgggagggatatcagctcggggcaggcatataaccttagacgttcaagggactgtacgttactcaaatt
cttgggcaattcaagaatccgtggacagttggttatgctgagagagttgagagaggttattccaaatatggattttagttccaaaagatcatcaca
gtgatcaatagtgagatcagacaagcttgggaatattttcgagatgtcgaatgacgtctgaacaaagctgttcttgaccttacaaaagattagatg
tatcttgtgcaggtttttcagtggaatggtgcagctggtgagttcagggacatgtaccctcttgagccagagactcctcagtttggccaaattggcaa
agatggagaagccatgtagacgcgcaggagacatgccattgttgataatcacgagcaccctgagtctactcatcttaccaataaatggtggca
agacgtagttgtccgaagagaagttcagtattaaaacttctgccttagggaggtccatgtcaaaccaattcatttcatccatttcccctgtatgaagg
gaaactatcttggcatcaaatggctcatctttattcttttcccattctcttggaagcactggctctgtttttggcattaataaccgctctctcctatttacgtc

- figure 5 (to be continued -

Figure 5 continued cacacgattggacatatgaagggctaggtctctcaaaacatcgtgttgcgtcacaaatacatcatagtagccaatgtgcacatcgccaaacctc
ggattgttcactatagtaaggagattcttgtcagctaaacgaagaacaaaggaaaacgcagtttcctcgtcaatatcatgcctctcaacccacac
gctcgtgagaagatcaagagggatcttcttgtcttcagggaaagcacccatatccaagaaacagtctcggatttcggtcgaggttttctagactt
tcttccatatgagcaaacactctgctctcatgagtttcatcagcagcttctcctcttaataacctcttcactacgccttcccaatatctttcaggtttgttttt
aacgaagcaccaagaactttcaaagataaaggtaaacctttacactcatcaacaacctgcttcaccaaatatttgttgaatggagaaggcggg
gacttttgttcgaaagcacagagacacaaaagagacattgcttcatctttctttaataattccacattgtaggtggttctaggatctgcaagcttgga
ccgtgacactactaaagtagtgcttccacgaattttagacatcagcctgtccaaggactcccttgtccaaacatcatcaagaatcactagcttccg
ttgatgaactccatcataaagaaattctcgtatacaagactccaaattctcaaaattcggagaccgtgacacagtcaaaaacaaaaccttattctt
aaagagtcctcgaacatcatcgtcctttgaaagctctattgcaagagtggttttccctgaaccgctcattccagagatcccaaacaaatgtgtatcc
gtaaacttaaacatcatctccttcacctttttcttccccaattccaataccgtctgaatctccggatcgcttaccgtctcaatctccatcatagtctccgg
aaacgacaaagaatcattccgctcagtcaacagtctatccatattcctctcaatcctgtcaccattgacccgtagatgacatacctcagcaagaa
caaagagcaaaatctggctgttgaggaaacgagatatttgtttctcgagatccttcatcttattcgcgtggtacacatgtttaaggttccacctattgc
atcttaaaaccttttcacatagctttcttgctttctccaagatctcatagaatactcccagttgagtttggtgatggttactcagctccgcgccactgtatt
ggatctccctgatcgttggttgaacgtctctgatcatcgtgatcagtcgttcggcgattcctttgcaactgtagactgtgttagctactagagcgagca
gctttaagagttgcgtcgtgatgtcgccggcgaaaagatctatgaacgaagccatggtaccagcctgctttttgtacaaacttgggtacggccgc
agatgggctgcacatacataacatatcaagatcagaacacacatatacacacacaaatacaatcaagtcaacaactccaaaaagtccagat
ctacatatatacatacgtaaataacaaaatcatgtaaataatcacaatcatgtaatccagatctatgcacatatatatatacacaattaataaaaa
aaatgatataacagatctatatctatgtatgtaacaacacaatcagatgagagaagtgatgttttcagatctgtatacatacaaacacaaacaga
tgaacaattgatacgtagatccatatgtatacgtacaattagctacacgattaaatgaaaaaaatcaacgatttcggattggtacacacaaacgc
aacaatatgaagaaattcatatctgattagatataaacataaccacgtgtagatacacagtcaaatcaacaaatttatagcttctaaacggatga
gatgaacaagataaagatattcacataaggcatacataagataagcagattaacaaactagcaataatacatacctaattaaaacaaggaat
aacagagagagagagagagagagagagatttaccttgaaaatgaagaggagaagagaggatttcttaaaattgggggtagagaaagaaag
atgatgaattgtgagaaaggagagatagaagggggggtgtatatataggctgtagaagattatttttgtgtttgaggcggtgaaggaagaggg
gatctgactatgacacgtttgcggttacgtatttcgataggagtctttcaacgcttaacgccgttactctatatgaccgtttgggccgtaacggggcc
gtttgttaacgctgatgttgattcttttctttctttctttcttcctttttttaaagaagcaattgtacaatcgttgctagctgtcaaacggataattcggatacgg
atatgcctatattcatatccgtaatttttggattcgaattctagaggatccgcccaaagcttggcgtaatcatggcaacttttctatacaaagttgatag
cttggcgtaatcgatatctttttaagggcgaattccagcacactggcggccgttactagtacggtacgatttaaataagcttggcgtaatcatggtc
atagctgtttcctactagatctgattgtcgtttcccgccttcagtttaaactatcagtgtttgacaggatatattggcgggtaaacctaagagaaaaga
gcgtttattagaataatcggatatttaaaagggcgtgaaaaggtttatccgttcgtccatttgtatgtccatggaacgcagtggcggttttcatggcttg
ttatgactgtttttttggggtacagtctatgcctcgggc
atccaagcagcaagcgcgttacgccgtgggtcgatgtttgatgttatggagcagcaacgatgttacgcagcagggcagtcgccctaaaacaa
agttaaacatcatgggggaagcggtgatcgccgaagtatcgactcaactatcagaggtagttggcgtcatcgagcgccatctcgaaccgacgt
tgctggccgtacatttgtacggctccgcagtggatggcggcctgaagccacacagtgatattgatttgctggttacggtgaccgtaaggcttgatg
aaacaacgcggcgagctttgatcaacgaccttttggaaacttcggcttcccctggagagagcgagattctccgcgctgtagaagtcaccattgtt
gtgcacgacgacatcattccgtggcgttatccagctaagcgcgaactgcaatttggagaatggcagcgcaatgacattcttgcaggtatcttcga
gccagccacgatcgacattgatctggctatcttgctgacaaaagcaagagaacatagcgttgccttggtaggtccagcggcggaggaactcttt
gatccggttcctgaacaggatctatttgaggcgctaaatgaaaccttaacgctatggaactcgccgcccgactgggctggcgatgagcgaaat
gtagtgcttacgttgtcccgcatttggtacagcgcagtaaccggcaaaatcgcgccgaaggatgtcgctgccgactgggcaatggagcgcctg
ccggcccagtatcagcccgtcatacttgaagctagacaggcttatcttggacaagaagaagatcgcttggcctcgcgcgcagatcagttggaa
gaatttgtccactacgtgaaaggcgagatcaccaaggtagtcggcaaataatgtctagctagaaattcgttcaagccgacgccgcttcgcggc
gcggcttaactcaagcgttagatgcactaagcacataattgctcacagccaaactatcaggtcaagtctgcttttattatttttaagcgtgcataata
agccctacacaaattgggagatatatcatgcatgaccaaaatcccttaacgtgagttttcgttccactgagcgtcagaccccgtagaaaagatc
aaaggatcttcttgagatcctttttttctgcgcgtaatctgctgcttgcaaacaaaaaaaccaccgctaccagcggtggtttgtttgccggatcaaga
gctaccaactctttttccgaaggtaactggcttcagcagagcgcagataccaaatactgtccttctagtgtagccgtagttaggccaccacttcaa
gaactctgtagcaccgcctacatacctcgctctgctaatcctgttaccagtggctgctgccagtggcgataagtcgtgtcttaccgggttggactca
agacgatagttaccggataaggcgcagcggtcgggctgaacggggggttcgtgcacacagcccagcttggagcgaacgacctacaccga
actgagatacctacagcgtgagctatgagaaagcgccacgcttcccgaagggagaaaggcggacaggtatccggtaagcggcagggtcg
gaacaggagagcgcacgagggagcttccagggggaaacgcctggtatctttatagtcctgtcgggtttcgccacctctgacttgagcgtcgattt
ttgtgatgctcgtcaggggggcggagcctatggaaaaacgccagcaacgcggcctttttacggttcctggccttttgctggccttttgctcacatgtt
ctttcctgcgttatcccctgattctgtggataaccgtattaccgcctttgagtgagctgataccgctcgccgcagccgaacgaccgagcgcagcga
gtcagtgagcgaggaagcggaagagcgcctgatgcggtattttctccttacgcatctgtgcggtatttcacaccgcatatggtgcactctcagtac
aatctgctctgatgccgcatagttaagccagtatacactccgctatcgctacgtgactgggtcatggctgcgccccgacacccgccaacacccg
ctgacgcgccctgacgggcttgtctgctcccggcatccgcttacagacaagctgtgaccgtctccgggagctgcatgtgtcagaggttttcaccgt
catcaccgaaacgcgcgaggcagggtgccttgatgtgggcgccggcggtcgagtggcgacggcgcggcttgtccgcgccctggtagattgc
ctggccgtaggccagccatttttgagcggccagcggccgcgataggccgacgcgaagcggcggggcgtagggagcgcagcgaccgaag
ggtaggcgctttttgcagctcttcggctgtgcgctggccagacagttatgcacaggccaggcgggttttaagagttttaataagttttaaagagtttta
ggcggaaaaatcgcctttttttctcttttatatcagtcacttacatgtgtgaccggttcccaatgtacggctttgggttcccaatgtacgggttccggttcc
caatgtacggctttgggttcccaatgtacgtgctatccacaggaaagagaccttttcgaccttttttcccctgctagggcaatttgccctagcatctgct
ccgtacattaggaaccggcggatgcttcgccctcgatcaggttgcggtagcgcatgactaggatcgggccagcctgccccgcctcctccttcaa
atcgtactccggcaggtcatttgacccgatcagcttgcgcacggtgaaacagaacttcttgaactctccggcgctgccactgcgttcgtagatcgt

- figure 5 to be continued -

Figure 5 continued cttgaacaaccatctggcttctgccttgcctgcggcgcggcgtgccaggcggtagagaaaacggccgatgccgggatcgatcaaaaagtaat
cggggtgaaccgtcagcacgtccgggttcttgccttctgtgatctcgcggtacatccaatcagctagctcgatctcgatgtactccggccgcccgg
tttcgctctttacgatcttgtagcggctaatcaaggcttcaccctcggataccgtcaccaggcggccgttcttggccttcttcgtacgctgcatggcaa
cgtgcgtggtgtttaaccgaatgcaggtttctaccaggtcgtctttctgctttccgccatcggctcgccggcagaacttgagtacgtccgcaacgtgt
ggacggaacacgcggccgggcttgtctcccttcccttcccggtatcggttcatggattcggttagatgggaaaccgccatcagtaccaggtcgta
atcccacacactggccatgccggccggccctgcggaaacctctacgtgcccgtctggaagctcgtagcggatcacctcgccagctcgtcggtc
acgcttcgacagacggaaaacggccacgtccatgatgctgcgactatcgcgggtgcccacgtcatagagcatcggaacgaaaaaatctggtt
gctcgtcgcccttgggcggcttcctaatcgacggcgcaccggctgccggcggttgccgggattctttgcggattcgatcagcggccgcttgccac
gattcaccggggcgtgcttctgcctcgatgcgttgccgctgggcggcctgcgcggccttcaacttctccaccaggtcatcacccagcgccgcgc
cgatttgtaccgggccggatggtttgcgaccgctcacgccgattcctcgggcttgggggttccagtgccattgcagggccggcagacaaccca
gccgcttacgcctggccaaccgcccgttcctccacacatggggcattccacggcgtcggtgcctggttgttcttgattttccatgccgcctcctttag
ccgctaaaattcatctactcatttattcatttgctcatttactctggtagctgcgcgatgtattcagatagcagctcggtaatggtcttgccttggcgtacc
gcgtacatcttcagcttggtgtgatcctccgccggcaactgaaagttgacccgcttcatggctggcgtgtctgccaggctggccaacgttgcagcc
ttgctgctgcgt
gcgctcggacggccggcacttagcgtgtttgtgcttttgctcatttctctttacctcattaactcaaatgagttttgatttaatttcagcggccagcgcct
ggacctcgcgggcagcgtcgccctcgggttctgattcaagaacggttgtgccggcggcggcagtgcctgggtagctcacgcgctgcgtgatac
gggactcaagaatgggcagctcgtacccggccagcgcctcggcaacctcaccgccgatgcgcgtgcctttgatcgcccgcgacacgacaa
aggccgcttgtagccttccatccgtgacctcaatgcgctgcttaaccagctccaccaggtcggcggtggcccatatgtcgtaagggcttggctgc
accggaatcagcacgaagtcggctgccttgatcgcggacacagccaagtccgccgcctggggcgctccgtcgatcactacgaagtcgcgcc
ggccgatggccttcacgtcgcggtcaatcgtcgggcggtcgatgccgacaacggttagcggttgatcttcccgcacggccgcccaatcgcggg
cactgccctggggatcggaatcgactaacagaacatcggccccggcgagttgcagggcgcgggctagatgggttgcgatggtcgtcttgcctg
acccgcctttctggttaagtacagcgataaccttcatgcgttccccttgcgtatttgtttatttactcatcgcatcatatacgcagcgaccgcatgacgc
aagctgttttactcaaatacacatcaccttttttagacggcggcgctcggtttcttcagcggccaagctggccggccaggccgccagcttggcatca
gacaaaccggccaggatttcatgcagccgcacggttgagacgtgcgcgggcggctcgaacacgtacccggccgcgatcatctccgcctcga
tctcttcggtaatgaaaaacggttcgtcctggccgtcctggtgcggtttcatgcttgttcctcttggcgttcattctcggcggccgccagggcgtcggc
ctcggtcaatgcgtcctcacggaaggcaccgcgccgcctggcctcggtgggcgtcacttcctcgctgcgctcaagtgcgcggtacagggtcga
gcgatgcacgccaagcagtgcagccgcctctttcacggtgcggccttcctggtcgatcagctcgcgggcgtgcgcgatctgtgccggggtgag
ggtagggcgggggccaaacttcacgcctcgggccttggcggcctcgcgcccgctccgggtgcggtcgatgattagggaacgctcgaactcg
gcaatgccggcgaacacggtcaacaccatgcggccggccggcgtggtggtaacgcgtg

METHOD OF INCREASING RESISTANCE AGAINST SOYBEAN RUST IN TRANSGENIC PLANTS BY ADR-1-GENE

CROSS-REFERENCE TO RELATED APPLICATIONS

This application is a continuation of U.S. patent application Ser. No. 13/817,512, which is a U.S. National Stage application of International Application No. PCT/IB2011/053615, filed Aug. 16, 2011, which claims the benefit of U.S. Provisional Patent Application No. 61/375,053, filed Aug. 19, 2010, and which claims priority to European Patent Application No. 10173393.9, filed Aug. 19, 2010; the entire contents of these application are incorporated herein by reference.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "71119_Seqlisting.txt", which was created on Aug. 16, 2017 and is 35,603 bytes in size. The subject matter of the Sequence Listing is incorporated herein in its entirety by reference.

The present invention relates to a method of increasing resistance against soybean rust in transgenic plants and/or plant cells. In these plants, the content and/or the activity of a ADR-1-protein is increased in comparison to the wild-type plants not including a recombinant ADR-1-gene.

Furthermore, the invention relates to transgenic plants and/or plant cells having an increased resistance against soybean rust and to recombinant expression vectors comprising a sequence that is identical or homologous to a sequence encoding a functional ADR-1-gene or fragments thereof.

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides.

Nowadays, the possibility of directly modifying the genetic disposition of a plant or pathogen is also open to man.

Resistance generally means the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms. In the latter case, the plant is resistant to the respective pathogen (Schopfer and Brennick, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular such a resistance works for different strains of the pathogen.

Fungi are distributed worldwide. Approximately 100 000 different fungal species are known to date. The rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant. The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact. Therefore the soybean rust fungus establishes a biotrophic interaction with soybean.

The biotrophic phytopathogenic fungi, such as many rusts, depend for their nutrition on the metabolism of living cells of the plants. The necrotrophic phytopathogenic fungi depend for their nutrition on dead cells of the plants. Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy will, for the purposes of the present invention, be referred to as being "heminecrotrohic".

Soybean rust has become increasingly important in recent times. The disease may be caused by the pathogenic rusts *Phakopsora pachyrhizi* (Sydow) and *Phakopsora meibomiae* (Arthur). They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant plants, four dominant genes Rpp1-4, which mediate resistance of soy to *P. pachyrhizi*, were discovered. The resistance was lost rapidly, as *P. pychyrhizi* develops new virulent races.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

Surprisingly the inventors found that the overexpression of the ADR-1-gene from *Arabidopsis* increases the resistance against soybean rust.

The object of the present invention is to provide a method of increasing resistance against soy bean rust in transgenic plants and/or transgenic plant cells. A further object is to provide transgenic plants resistant against soybean rust, a method for producing such plants as well as a vector construct useful for the above methods. This object is achieved by the subject-matter of the main claims. Preferred embodiments of the invention are defined by the features of the sub-claims.

The present invention may be understood more readily by reference to the following detailed description of the preferred embodiments of the invention and the examples included herein. Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar or higher functional activity as the unmodified protein coded by the unmodified nucleic acid from which they are derived. In particular homologues of a nucleic acid emcompass substitutions on the basis of the degenerative amino acid code.

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or β-sheet structures).

On the nucleic acid level a substitution refers a replacement of nucleic acid with other nucleic acids, wherein the protein coded by the modified nucleic acid has a similar function. In particular homologues of a nucleic acid emcompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

| Examples of conserved amino acid substitutions | |
|---|---|
| Residue | Conservative Substitutions |
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

As used herein the terms "soybean rust-resistance", "resistant to a soybean rust", "soybean rust-resistant", "rust-resistance", "resistant to a rust", "rust-resistant", "fungal-resistance", "resistant to a fungus" and/or "fungal-resistant" mean reducing or preventing an infection by soybean rust, in particular *Phakopsora pachyrhizi* (Sydow) and *Phakopsora meibomiae* (Arthur). The term "resistance" refers to soybean resistance. Resistance does not imply that the plant necessarily has 100% resistance to infection. In preferred embodiments, the resistance to infection by soy bean rust in a resistant plant is greater than 10%, 20%, 30%, 40%, 50%, 60%, 70%, 80%, 90%, or 95% in comparison to a wild type plant that is not resistant to soybean rust. Preferably the wild type plant is a plant of a similar, more preferably identical, genotype as the plant having increased resistance to the soybean rust, but does not comprise a recombinant nucleic acid of the ADR-1-gen, functional fragments thereof and/or a nucleic acid capable of hybridizing with ADR-1-gene. Preferably, the wild type plant does not comprise an endogenous nucleic acid of the ADR-1-gen, functional fragments thereof and/or a nucleic acid capable of hybridizing with ADR-1-gene.

The terms "soybean rust-resistance", "resistant to a soybean rust", "soybean rust-resistant", "rust-resistance", "resistant to a rust", "rust-resistant", fungal-resistance, resistant to a fungus" and/or "fungal-resistant" as used herein refers to the ability of a plant, as compared to a wild type plant, to avoid infection by soybean rust, to kill rust, to hamper, to reduce, to delay, to stop the development, growth and/or multiplication of soybean rust. The level of fungal resistance of a plant can be determined in various ways, e.g.

by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P-meibomiae* PHYTOPATHOLOGY 92(2) 217-227). Preferably, the soybean rust resistance is nonhost-resistance. Nonhost-resistance means that the plants are resistant to at least 80%, at least 90%, at least 95%, at least 98%, at least 99% and preferably 100% of the strains of the soybean rust pathogen, preferably the strains of *Phakopsora pachyrhizi.*

The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term stringency conditions refers to conditions, wherein 100 contigous nucleotides or more, 150 contigous nucleotides or more, 200 contigous nucleotides or more or 250 contigous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M $NaPO_4$, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M $NaPO_4$, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M $NaPO_4$, 1 mM EDTA at 50° C. with washing in 0.1×SSC, 0.1% SDS at 50° C. or 65° C., preferably 65° C. Preferably, the complementary nucleotides hybridize with a fragment or the whole ADR-1-gen. Preferably, the complementary polynucleotide hybridizes with parts of the ADR-1-gene capable to provide soybean rust resistance.

As used herein, the term "ADR-1-gene" refers to a gene having at least 60% identity with SEQ-ID-No. 1 or with a sequence coding for a protein having at least 60% identity with SEQ-ID-No. 2 and/or functional fragments thereof. In one embodiment homologues of the ADR-1-gene have, at the DNA level and/or protein level, at least 70%, preferably of at least 80%, especially preferably of at least 90%, quite especially preferably of at least 95%, quite especially preferably of at least 98% or 100% identity over the entire DNA region or protein region given in a sequence specifically disclosed herein and/or a functional fragment thereof.

As used herein, the term "ADR-1-protein" refers to a protein having at least 60% identity to a sequence coding for a protein having SEQ-ID-No. 2 and/or a fragment thereof. In one embodiment homologues of the ADR-1-protein have at least 70%, preferably of at least 80%, especially preferably of at least 90%, quite especially preferably of at least 95%, quite especially preferably of at least 98% or 100% identity over the entire protein region given in a sequence specifically disclosed herein and/or a functional fragment thereof.

"Identity" or "homology" between two nucleic acids and/or refers in each case over the entire length of the nucleic acid.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/iindex.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

Sequence identity between the nucleic acid useful according to the present invention and the ADR-1 gene may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). At least 60% sequence identity, preferably at least 70% sequence identity, 80% 90%, 95%, 98% sequence identity, or even 100% sequence identity, with the nucleic acid having SEQ-ID-No. 1 is preferred.

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the recombinant ADR1-gen. In one embodiment, the seeds are true breeding for an increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" ADR-1-gen" refers to the gene in question as found in a plant in its natural form (i.e., without there being any human intervention). Recombinant ADR-1-gene refers to the same gene (or a substantially homologous nucleic acid/gene) in an isolated form subsequently (re)introduced into a plant (a transgene). For example, a transgenic plant containing such a transgene may encounter a substantial increase of the transgene expression in addition to the expression of the endogenous gene. The isolated gene may be isolated from an organism or may be manmade, for example by chemical synthesis. A transgenic plant according to the present invention includes a recombinant ADR-1-gene integrated at any genetic loci and optionally the plant may also include the endogenous gene within the natural genetic background. Preferably, the plant does not include an endogenous ADR-1-gene.

For the purposes of the invention, "recombinant" means with regard to, for example, a nucleic acid sequence, an expression cassette or a vector construct comprising the ADR-1-gene, all those constructions brought about by gentechnological methods in which either (a) the ADR-1-sequences encoding ADR-1-proteins, or
(b) genetic control sequence(s) which is operably linked with the ADR-1-nucleic acid sequence according to the invention, for example a promoter, or
(c) a) and b)

are not located in their natural genetic environment or have been modified by gentechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp.

A naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by non-natural, synthetic ("artificial") methods such as, for example, mutagenic treatment. Suitable methods are described, for example, in U.S. Pat. No. 5,565,350 or WO 00/15815. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

It shall further be noted that in the context of the present invention, the term "isolated nucleic acid" or "isolated protein" may in some instances be considered as a synonym for a "recombinant nucleic acid" or a "recombinant protein", respectively and refers to a nucleic acid or protein that is not located in its natural genetic environment and/or that has been modified by gentechnical methods.

A transgenic plant for the purposes of the invention is thus understood as meaning that the ADR-1-nucleic acids are not present in the genome of the original plant and/or are present in the genome of the original plant or an other plant not at their natural locus of the genome of the original plant. Natural locus means the location on a specific chromosome, preferably the location between certain genes, more preferably the same sequence background as in the original plant. It being possible for the nucleic acids to be expressed homologously or heterologously. Transgenic is preferably understood as meaning the expression of the nucleic acids according to the invention not in the original plant and/or at an unnatural locus in the genome, i.e. heterologous expression of the nucleic acids takes place.

As used herein, the term "transgenic" preferably refers to any plant, plant cell, callus, plant tissue, or plant part that contains all or part of the ADR-1-gene not at their natural locus. Preferably, all or part of the ADR-1-gene is stably integrated into a chromosome or stable extra-chromosomal element, so that it is passed on to successive generations.

The term "expression" or "gene expression" or "increase of content" means the transcription of a specific gene or specific genes or specific genetic vector construct. The term "expression" or "gene expression" in particular means the transcription of a gene or genes or genetic vector construct into structural RNA (rRNA, tRNA) or mRNA with or without subsequent translation of the latter into a protein. The process includes transcription of DNA and processing of the resulting mRNA product.

The term "increased expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If protein expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

The term "functional fragment" refers to any nucleic acid and/or protein which comprises merely a part of the full-length nucleic acid and/or fulllength protein but still provides the same function, i.e. soybean rust resistance when expressed in a plant. Preferably, the fragment comprises at least 50%, at least 60%, at least 70%, at least 80%, at least 90% at least 95%, at least 98%, at least 99% of the original sequence. Preferably, the functional fragment comprises contigous nucleic acids or amino acids as in the original nucleic acid and/or original protein.

In one embodiment the fragment of the ADR-1-nucleic acid has an identity as defined above over a length of at least 500, at least 1000, at least 1500, at least 2000 nucleotides to the ADR-1-gene.

The term "similar functional activity" or "similar function" in this context means that any homologue and/or fragment provide soybean rust resistance when expressed in a plant. Preferably similar functional activity means at least 50%, at least 60%, at least 70%, at least 80%, at least 90%, at least 95%, at least 98%, at least 99% or 100% or higher of the soybean rust resistance compared with functional activity provided by the recombinant expression of the ADR-1-nucleotide sequence SEQ-ID No. 1 and/or recombinant ADR-1-protein sequence SEQ-ID No. 2.

The term "increased activity" as used herein means any protein having increased activity provides an increased soybean rust resistance compared with the wildtype plant merely expressing the endogenous ADR-1-gene. For the purposes of this invention, the original wild-type expression level might also be zero (absence of expression).

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

The transgenic plant cells may be transformed with one of the above described vector constructs. Suitable methods for transforming or transfecting host cells including plant cells are well known in the art of plant biotechnology. Any method may be used to transform the recombinant expression vector into plant cells to yield the transgenic plants of the invention. General methods for transforming dicotyledenous plants are disclosed, for example, in U.S. Pat. Nos. 4,940,838; 5,464,763, and the like. Methods for transforming specific dicotyledenous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells. The genetically modified plant cells can be regenerated via all methods with which the skilled worker is familiar. Suitable methods can be found in the abovementioned publications by S. D. Kung and R. Wu, Potrykus or Hofgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention provides a method for increasing rust resistance in plants and/or plant cells, wherein the content and/or activity of at least one ADR-1-protein is increased in comparison to wild type plants and/or plant cells.

In one embodiment of the method the ADR-1 protein is encoded by a recombinant nucleic acid having at least 60%, at least 70%, at least 80%, at least 90%, at least 95%, at least 98% identity or 100% identity with SEQ ID No. 1, a functional fragment thereof and/or a nucleic acid capable of hybridizing with such a nucleic acid and/or is a protein having at least 60%, at least 70%, at least 80%, at least 90%, at least 95%, at least 98% identity or 100% identity with SEQ ID No. 2, a functional fragment thereof, an orthologue and/or a paralogue thereof.

In one embodiment the method comprises (a) stably transforming a plant cell with a expression cassette comprising (i) a recombinant nucleic acid sequence having at least 60%, at least 70%, at least 80%, at least 90% a least 95%, at least 98% identity or 100% identity with SEQ ID No. 1 and/or a functional fragment thereof in functional linkage with a promoter and/or (ii) a recombinant nucleic acid coding for a protein having at least 60%, at least 70%, at least 80%, at least 90%, at least 95%, at least 98% identity or 100% with SEQ ID No. 2, a functional fragment thereof, an orthologue and/or a paralogue thereof, (b) regenerating the plant from the plant cell; and (c) expressing said nucleic acid sequence which codes for a ADR-1-protein in an amount and for a period sufficient to generate or to increase a soybean rust resistance in said plant.

In one embodiment the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. medullare Alef. emend. C.O. Lehm), sugar pea (*Pisum sativum* L. convar. axiphium Alef emend. C.O. Lehm), also called snow pea, edible-podded pea or mangetout, (*Pisum granda sneida* L. convar. sneidulo *P. shneiderium*)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis*

(Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.)); goa bean (*Psophocarpus tetragonolobus* (L.) DC.), African yam bean (*Sphenostylis stenocarpa* (Hochst. ex A. Rich.) Harms), Egyptian black bean, *dolichos* bean, *lablab* bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.)).

Preferable the plant according to the present invention is soy.

Further, the present invention comprises a recombinant vector construct comprising:

(a) a recombinant nucleic acid
    (i) having at least 60%, at least 70%, at least 80%, at least 90%, at least 95%, at least 98% or 100% identity with SEQ ID No. 1, a functional fragment thereof and/or a nucleic acid capable of hybridizing with such a nucleic acid and/or
    (ii) comprising a recombinant nucleic acid coding for a protein having at least 60%, at least 70%, at least 80%, at least 90%, at least 95%, at least 98% identity or 100% with SEQ ID No. 2, a functional fragment thereof, an orthologue and/or a paralogue, operably linked with
(b) a promoter and
(c) a transcription termination sequence.

With respect to a recombinant vector construct and/or the recombinant nucleic acid, the term "functional linked" is intended to mean that the recombinant nucleic acid is linked to the regulatory sequence, including promoters, terminator regulatory sequences, enhancers and/or other expression control elements (e.g., polyadenylation signals), in a manner which allows for expression of the ADR-1-gene (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of RNA desired, and/or the like. The vector constructs of the invention can be introduced into plant host cells to thereby produce ADR-1-protein in order to prevent and/or reduce soybean rust infections.

Promoters according to the present invention may be constitutive, inducible, in particular pathogen-inducible, developmental stage-preferred, cell type-preferred, tissue-preferred and/or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like. Promoters that express the RNA in a cell that is contacted by fungus, in particular soybean rust, are preferred. Alternatively, the promoter may drive expression of the RNA in a plant tissue remote from the site of contact with the fungus, and the RNA may then be transported by the plant to a cell that is contacted by the fungus, in particular cells of, and/or close by fungal infected sites.

Preferably, the promoter is a constitutive promoter, root-specific promoter, mesophyll-specific promoter, and/or a fungal-inducible promoter. A promoter is inducible, if its activity, measured on the amount of RNA produced under control of the promoter, is at least 30%, 40%, 50% preferably at least 60%, 70%, 80%, 90% more preferred at least 100%, 200%, 300% higher in its induced state, than in its un-induced state. A promoter is cell-, tissue- or organ-specific, if its activity, measured on the amount of RNA produced under control of the promoter, is at least 30%, 40%, 50% preferably at least 60%, 70%, 80%, 90% more preferred at least 100%, 200%, 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds.

Developmental stage-preferred promoters are preferentially expressed at certain stages of development. Tissue and organ preferred promoters include those that are preferentially expressed in certain tissues or organs, such as leaves, roots, seeds, and/or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and/or seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No.

WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene)

Promoters useful according to the invention include, but are not limited to, are the major chlorophyll a/b binding protein promoter, histone promoters, the Ap3 promoter, the β-conglycin promoter, the napin promoter, the soylectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic and/or other natural promoters.

Epidermisspezific promoters may be selected from the group consisting of:

- WIR5 (=GstA1); acc. X56012; Dudler & Schweizer,
- GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998),
- GLP2a, acc. AJ237942, Schweizer P., Christoffel A. and Dudler R., Plant J. 20, 541 (1999);
- Prx7, acc. AJ003141, Kristensen B. K., Ammitzböll H., Rasmussen S. K. and Nielsen K. A., Molecular Plant Pathology, 2(6), 311 (2001);
- GerA, acc. AF250933; Wu S., Druka A., Horvath H., Kleinhofs A., Kannangara G. and von Wettstein D., Plant Phys Biochem 38, 685 (2000);
- OsROC1, acc. AP004656
- RTBV, acc. AAV62708, AAV62707; Klöti A., Henrich C., Bieri S., He X., Chen G., Burkhardt P. K., Wünn J., Lucca P., Hohn T., Potrykus I. and Fütterer J., PMB 40, 249 (1999);
- Chitinase ChtC2-Promoter from potato (Ancillo et al., Planta. 217(4), 566, (2003));
- AtProT3 Promoter (Grallath et al., Plant Physiology. 137(1), 117 (2005));
- SHN-Promoters from *Arabidopsis* (AP2/EREBP transcription factors involved in cutin and wax production) (Aarón et al., Plant Cell. 16(9), 2463 (2004)); and/or
- GSTA1 from wheat (Dudler et al., WP2005306368 and Altpeter et al., Plant Molecular Biology. 57(2), 271 (2005)).

Mesophyllspezific promoters may be selected from the group consisting of:

- PPCZm1 (=PEPC); Kausch A. P., Owen T. P., Zachwieja S. J., Flynn A. R. and Sheen J., Plant Mol. Biol. 45, 1 (2001);
- OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993);
- OsPPDK, acc. AC099041;
- TaGF-2.8, acc. M63223; Schweizer P., Christoffel A. and Dudler R., Plant J. 20, 541 (1999);
- TaFBPase, acc. X53957;
- TaWIS1, acc. AF467542; US 200220115849;
- HvBIS1, acc. AF467539; US 200220115849; and/or
- ZmMIS1, acc. AF467514; US 200220115849;

Pathogen-induceable promoters may be seleted from the group consisting of

- HvPR1a, acc. X74939; Bryngelsson et al., Mol. Plant Microbe Interacti. 7 (2), 267 (1994);
- HvPR1b, acc. X74940; Bryngelsson et al., Mol. Plant Microbe Interact. 7(2), 267 (1994);
- vB1,3gluc; acc. AF479647;
- HvPrx8, acc. AJ276227; Kristensen et al., Molecular Plant Pathology, 2(6), 311 (2001); and/or
- HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of

- PcUbi promoter from parsley (WO 03/102198)
- CaMV 35S promoter: Cauliflower Mosaic Virus 35S promoter (Benfey et al. 1989 EMBO J. 8(8): 2195-2202),
- STPT promoter: *Arabidopsis thaliana* Short Triose phosphat translocator promoter (Accession NM_123979)
- Act1 promoter:—*Oryza sativa* actin 1 gene promoter (McElroy et al. 1990 PLANT CELL 2(2) 163-171 a) and/or
- EF1A2 promoter: *Glycine max* translation elongation factor EF1 alpha (US 20090133159).

One type of recombinant vector construct is a "plasmid," which refers to a circular double stranded DNA loop into which additional DNA segments can be ligated. Another type of vector is a viral vector, wherein additional DNA segments can be ligated into the viral genome. Certain recombinant vector constructs are capable of autonomous replication in a host plant cell into which they are introduced. Other recombinant vector constructs are integrated into the genome of a host plant cell upon introduction into the host cell, and thereby are replicated along with the host genome. In particular, the vector construct is capable of directing the expression of gene to which the vectors is functional linked. However, the invention is intended to include such other forms of expression vector constructs, such as viral vectors (e.g., potato virus X, tobacco rattle virus, and/or Gemini virus), which serve equivalent functions.

A preferred vector construct comprises the sequence having SEQ-ID-No. 9.

The present invention further provides a transgenic soy plant, plant part or plant cell transformed with a vector construct comprising the ADR-1-gene. Preferably, the vector construct is a vector construct as defined above.

Harvestable parts of the transgenic soy bean plant according to the present invention are part of the invention. The harvestable parts may be seeds, roots, leaves and/or flowers comprising the ADR-1-gene. Preferred are soy beans comprising the transgenic ADR-1-gene.

Products derived from transgenic soy plant according to the present invention, parts thereof or harvestable parts thereof are part of the invention.

The present invention also includes methods for the production of a product comprising a) growing the plants of the invention and b) producing said product from or by the plants of the invention and/or parts thereof, e.g. seeds, of these plants. In a further embodiment the method comprises the steps a) growing the plants of the invention, b) removing the harvestable parts as defined above from the plants and c) producing said product from or by the harvestable parts of the invention.

In one embodiment the method for the production of a product comprises a) growing the plants of the invention or obtainable by the methods of invention and b) producing said product from or by the plants of the invention and/or parts, e.g. seeds, of these plants.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic or pharmaceutical. Foodstuffs are regarded as compositions used for nutrition or for supplementing nutrition. Animal feedstuffs and animal feed supplements, in particular, are regarded as foodstuffs.

A preferred product is soybean meal and/or soybean oil.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one ore more agricultural products to a large extent.

The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more nucleic acids, thus creating a “stack” of transgenes in the plant and/or its progeny. The seed is then planted to obtain a crossed fertile transgenic plant comprising the nucleic acid of the invention. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the recombinant nucleic acid comprising the transgenic ADR-1-gene.

According to the present invention, the introduced recombinant nucleic acid may be maintained in the plant cell stably if it is incorporated into a non-chromosomal autonomous replicon or integrated into the plant chromosomes. Whether present in an extra-chromosomal non-replicating or replicating vector construct or a vector construct that is integrated into a chromosome, the recombinant nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

According to the present invention the ADR-1-gene is capable to increase the protein quantity or function of the ADR-1-protein in plants cell and/or the fungus. In preferred embodiments, the increase in the protein quantity or function of the ADR-1-protein takes place in a constitutive or tissue-specific manner. In especially preferred embodiments, an essentially pathogen-induced increase in the protein quantity or protein function takes place, for example by recombinant expression of the ADR-1-gene under the control of a fungal-induceable promoter. In particular, the expression of the ADR-1-gene takes place on fungal infected sites, where, however, preferably the expression of the ADR-1-gene remains essentially unchanged in tissues not infected by fungus. In preferred embodiments, the protein amount of the ADR-1-protein in the plant and/or the fungus is increased by at least 10%, at least 20%, at least 30%, at least 40%, at least 50%, at least 60%, at least 70%, at least 80%, at least 90%, or at least 95% or more in comparison to a wild type plant that is not transformed with the ADR-1-nucleic acid. Preferably the wild type plant is a plant of a similar, more preferably identical genotype as the plant transformed with the ADR-1-nucleic acid.

Further the present invention provides a method for the production of a transgenic plant having increased resistance against rust, comprising (a) introducing a recombinant vector construct as defined above into a plant or plant cell, (b) regenerating the plant from the plant cell and (c) expressing a protein (i) having at least 60%, at least 70%, at least 80%, at least 90% at least 95%, at least 98% or 100% identity with SEQ ID No. 2, a functional fragment thereof, an orthologue and/or paralogue thereof and/or (ii) a protein coded by a nucleic acid having at least 60%, at least 70%, at least 80%, at least 90%, at least 95%, at least 98% identity or 100% with SEQ ID No. 1, a functional fragment thereof and/or a nucleic acid capable of hybridizing with such a nucleic acid.

The ADR-1-nucleic acid sequence may comprise a N-terminal coiled-coil motif, a nucleotide binding site and/or a C-terminal leucine-rich repeat motif.

Preferably, the N-terminal coiled-coil motif has at least 70%, at least 80%, at least 90%, at least 95%, at least 98% or 100% identity with SEQ-ID-No 3.

Preferably, the nucleotide binding site has at least 70%, at least 80%, at least 90%, at least 95%, at least 98% or 100% identity with SEQ-ID-No 5.

Preferably, the C-terminal leucine-rich repeat motif has at least 70%, at least 80%, at least 90%, at least 95%, at least 99% or 100% identity with SEQ-ID-No 7.

The ADR-1-protein sequence preferably comprises a N-terminal coiled-coil motif, a nucleotide binding site and/or a C-terminal leucine-rich repeat motif.

Preferably, N-terminal coiled-coil motif has at least 70%, at least 80%, at least 90%, at least 95%, at least 98% or 100% identity with SEQ-ID-No 4.

Preferably, the nucleotide binding site has at least 70%, at least 80%, at least 90%, at least 95%, at least 98% or 100% identity with SEQ-ID-No 6.

Preferably, the C-terminal leucine-rich repeat motif has at least 70%, at least 80%, at least 90%, at least 95%, at least 98% or 100% identity with SEQ-ID-No 8.

All definitions given to terms used in specific type of category (method for producing a plant and/or part thereof resistant to soybean rust, transgenic plant cell, vector construct, use of the vector construct etc.) may be also applicable for the other categories.

FIGURES

FIG. 1 shows the full-length-sequence of the ADR-1-gene from *Arabidopsis thaliana* having SEQ-ID-No. 1.

FIG. 2 shows the sequence of the ADR-1-protein (SEQ-ID-2).

FIG. 3 shows different motivs on the ADR-1-gene (SEQ-ID-Nos. 3, 5, 7) and of the ADR-1-protein (SEQ-ID-Nos. 4, 6, 8).

FIG. 5 shows the whole nucleotide sequence of one vector construct according to the present invention (SEQ-ID-No. 9).

Figure 7:
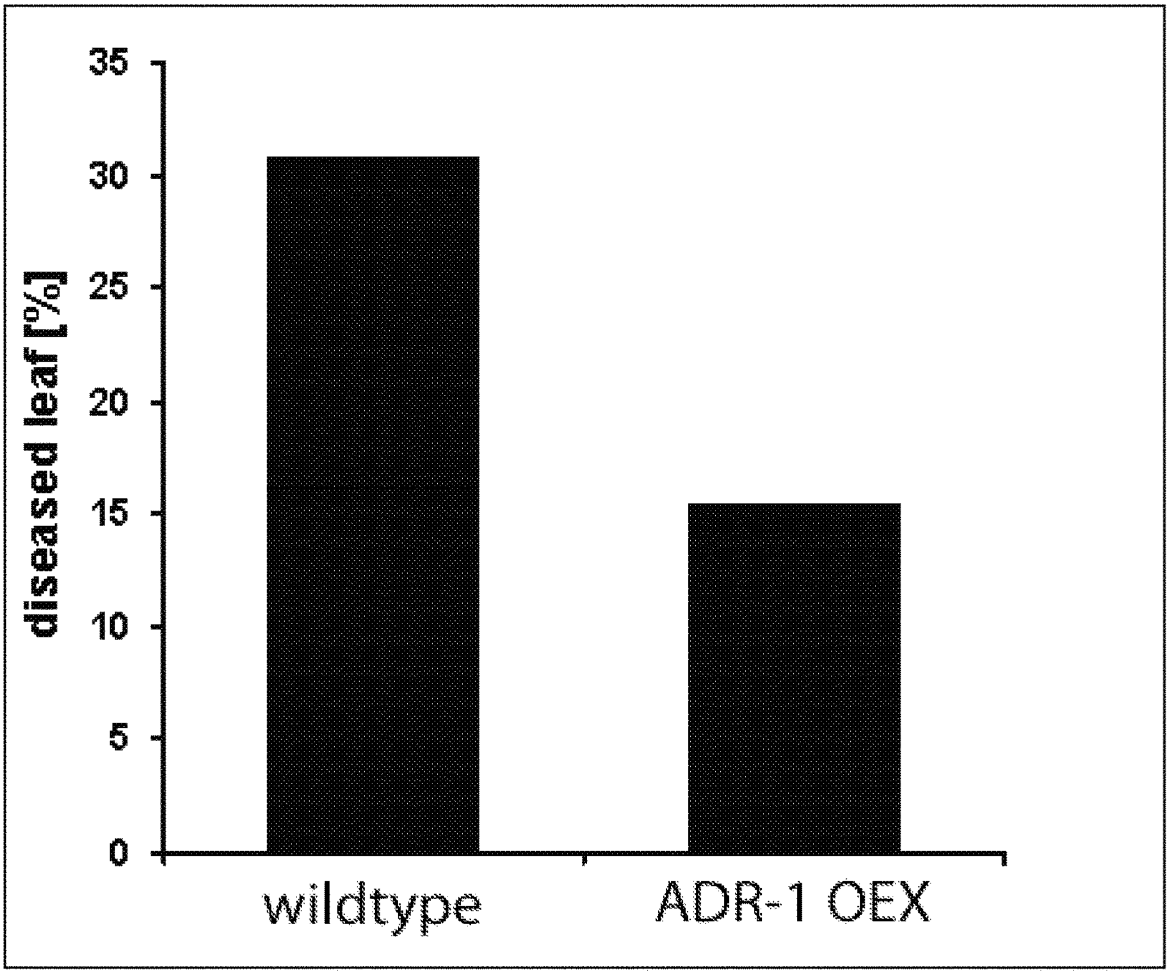

FIG. 7 shows the result of the scoring of 22 transgenic soy plants expressing the ADR-1 overexpression vector construct. T0 soybean plants expressing ADR-1 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 22 soybean $T_0$ plants expressing ADR-1 (expression checked by RT-PCR) were evaluated in parallel to non-transgenic control plants. The median of the diseased leaf area is shown in FIG. 7. Overexpression of ADR-1 strongly reduces the diseased leaf area in comparison to non-transgenic control plants.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of ADR-1 Overexpression Vector Construct

The overexpression ADR-1 vector construct (FIGS. 4 and 5) was prepared as follows:

Unless otherwise specified, standard methods as described in Sambrook et al., Molecular Cloning: A laboratory manual, Cold Spring Harbor 1989, Cold Spring Harbor Laboratory Press are used.

cDNA was produced from *Arabidopsis thaliana* (ecotype Col-0) RNA by using the Superscript II cDNA synthesis kit (Invitrogen). All steps of cDNA preparation and purification were performed according as described in the manual.

The SEQ-ID-No.1-sequence was amplified from cDNA by PCR as described in the protocol of the Phusion hot-start, Pfu Ultra, Pfu Turbo or Herculase DNA polymerase (Stratagene). The composition for the protocol of the Pfu Ultra, Pfu Turbo or Herculase DNA polymerase was as follows: 1×PCR buffer, 0.2 mM of each dNTP, 100 ng cDNA of *Arabidopsis thaliana* (var Columbia-0), 50 pmol forward primer, 50 pmol reverse primer, 1 u Phusion hot-start, Pfu Ultra, Pfu Turbo or Herculase DNA polymerase.

The amplification cycles were as follows:

1 cycle of 60 seconds at 98° C., followed by 35 cycles of in each case 10 seconds at 98° C., 30 seconds at 60° C. and 60 seconds at 72° C., followed by 1 cycle of 10 minutes at 72° C., then 4° C.

The following primer sequences were used to specifically amplify the ADR-1 full-length ORF for cloning purposes:

```
i) foward primer:
                              (SEQ ID NO: 10)
5'CCGGTACCATGGCTTCGTTCATAGAT-3'

ii) reverse primer:
                              (SEQ ID NO: 11)
5'-TTGTCGACCTAATCGTCAAGCCAATC-3'
```

The amplified fragments were digested using the restriction enzymes Acc65l and SalI (NEB Biolabs) and ligated in a Acc65l/SalI digested Gateway pENTRY vector (Invitrogen, Life Technologies, Carlsbad, Calif., USA) in a way that the full-length ADR-1 fragment is located in sense direction between the attL1 and attL2 recombination sites.

Figure 4:
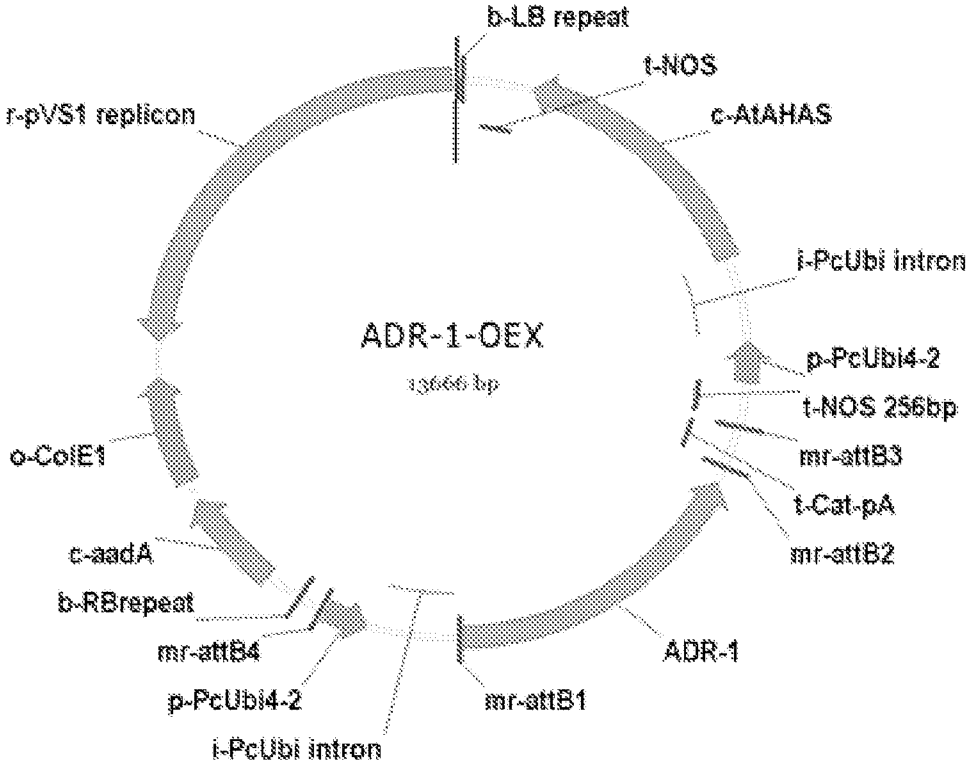
FIG. 4 shows a schema of one vector construct useful according to the present invention.

To obtain the binary plant transformation vector, a triple LR reaction (Gateway system, (Invitrogen, Life Technologies, Carlsbad, Calif., USA) was performed according to manufacturers protocol by using a pENTRY-A vector containing a parsley ubiquitine promoter, the ADR-1 in a pENTRY-B vector and a pENTRY-C vector containing a t-Nos terminator. As target a binary pDEST vector was used which is composed of: (1) a Kanamycin resistance cassette for bacterial selection (2) a pVS1 origin for replication in Agorbacteria (3) a pBR322 origin of replication for stable maintenance in *E. coli* and (4) between the right and left border an AHAS selection under control of a pcUbi-promoter (FIG. 4). The recombination reaction was transformed into *E. coli* (DH5alpha), mini-prepped and screened by specific restriction digestions. A positive clone from each vector construct was sequenced and submitted soy transformation.

Example 3 Soy Transformation

The ADR-1 expression vector construct (see example 2) was transformed into soy.

3.1 Sterilization and Germination of Soy Seeds

Virtually any seed of any soy variety can be employed in the method of the invention. A variety of soycultivar (including Jack, Williams 82, and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 μM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 μEinstein/$m^2$s) at 25 degree C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings (Method A, see example 3.3.1 and 3.3.2) or leaf explants (Method B, see example 3.3.3), the seedlings were then ready for transformation.

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium YEP media: 10 g yeast extract. 10 g Bacto Peptone. 5 g NaCl. Adjust pH to 7.0, and bring final volume to 1 liter with H2O, for YEP agar plates add 20 g Agar, autoclave) and incubating at 25.degree C. until colonies appeared (about 2 days). Depending on the selectable marker genes present on the Ti or Ri plasmid, the binary vector, and the bacterial chromosomes, different selection compounds were be used for *A. tumefaciens* and *rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25.degree. C.) until an OD.sub.600 between 0.8-1.0 is reached (approximately 2 d). Working glycerol stocks (15%) for transformation are prepared and one-ml of *Agrobacterium* stock aliquoted into 1.5 ml Eppendorf tubes then stored at −80.degree C.

The day before explant inoculation, 200 ml of YEP were inoculated with 5 .mu.l to 3 ml of working *Agrobacterium* stock in a 500 ml Erlenmeyer flask. The flask was shaked overnight at 25.degree. C. until the OD.sub.600 was between 0.8 and 1.0. Before preparing the soyexplants, the Agrobacteria were pelleted by centrifugation for 10 min at 5,500.times.g at 20.degree. C. The pellet was resuspended in liquid CCM to the desired density (OD.sub.600 0.5-0.8) and placed at room temperature at least 30 min before use.

3.3—Explant Preparation and Co-Cultivation (Inoculation)

3.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15.times.100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soyacv L00106CN, 93-41131 and Jack were germinated in 1/10 MS salts or a similar composition medium with or without cytokinins for 4.about.8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the GUS marker gene and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for enhancing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong GUS expression were recovered. Soyplants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any preformed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soyexplants. Wrap five plates with Parafilm™. "M" (American National Can, Chicago, Ill., USA) and incubate for three to five days in the dark or light at 25.degree. C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soyexplants. Plates were wrapped with Parafilm™. "M" (American National Can, Chicago, Ill., USA) and incubated for two to three days in the dark at 25.degree. C.

3.4—Shoot Induction

After 3 to 5 days co-cultivation in the dark at 25.degree. C., the explants were rinsed in liquid SIM medium (to remove excess *Agrobacterium*) (SIM, see Olhoft et al 2007 A novel *Agrobacterium rhizogenes*-mediated transformation method of soyusing primary-node explants from seedlings In Vitro Cell. Dev. Biol.—Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25.degree. C. under 18 h light/6 h dark cycle at 70-100.mu.E/m.sup.2s. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al 2007 A novel *Agrobacterium rhizogenes*-mediated transformation method of soyusing primary-node explants from seedlings In Vitro Cell. Dev. Biol.—Plant (2007) 43:536-549) that stimulates shoot elongation of the shoot primordia. This medium may or may not contain a selection compound.

After every 2 to 3 weeks, the explants were transfer to fresh SEM medium (preferably containing selection) after carefully removing dead tissue. The explants should hold together and not fragment into pieces and retain somewhat healthy. The explants were continued to be transferred until the explant dies or shoots elongate. Elongated shoots>3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

Transient GUS expression after 5 days of co-cultivation with *Agrobacterium tumefaciens* was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GUS gene was stable after 14 days on SIM, implying integration of the T-DNA into the soygenome. In addition, preliminary experiments resulted in the formation of GUS positive shoots forming after 3 weeks on SIM.

[For Method C, the average regeneration time of a soy-plantlet using the propagated axillary meristem protocol was 14 weeks from explant inoculation. Therefore, this method has a quick regeneration time that leads to fertile, healthy soyplants.

Example 4: Pathogen Assay 4.1. Recovery of Clones 2-3 clones per TO event were potted into small 6 cm pots. For recovery the clones were kept for 12-18 days in the Phytochamber (16 h-day-und 8 h-night-Rhythm at a temperature of 16° bis 22° C. und a humidity of 75% were grown).

4.2 Inoculation

The rust fungus is a wild isolate from Brazil. The plants were inoculated with *P.pachyrhizi.*

In order to obtain appropriate spore material for the inoculation, soyleaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-$H_2O$ solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of 1-5×$10^5$ spores/ml. For the microscopy, a density of >5×105 spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5 Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were ished 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6 Evaluation of the Susceptibility to Soybean Rust

Figure 6:
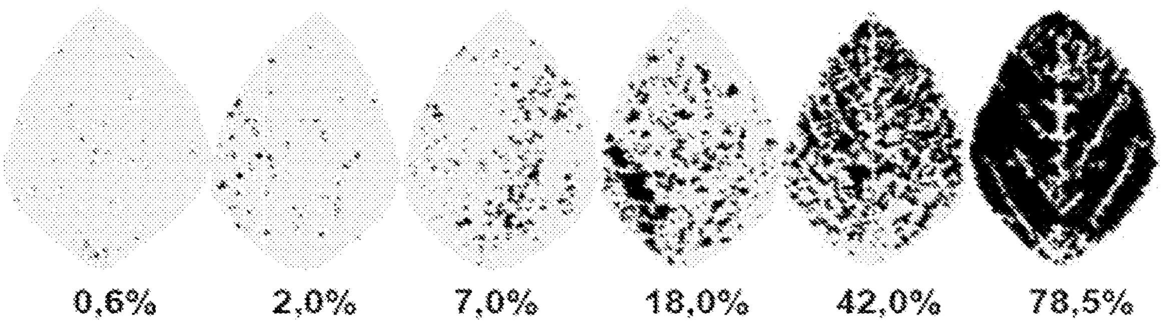
FIG. 6 shows the scoring system used to determine the level of diseased leaf area of wildtype and transgenic (ADR-1 expressing) soy plants against the rust fungus *P. pachyrhizi*.

The progression of the soybean rust disease was scored by the estimation of the diseased area (area which was covered by sprouting uredinia) on the backside (abaxial side) of the leaf. Additionally the yellowing of the leaf was taken into account. (for scheme see FIG. 6)

T0 soybean plants expressing ADR-1 protein were inoculated with spores of *Phakopsora pachyrhizi*. The macroscopic disease symptoms of soyagainst *P. pachyrhizi* of 22 T0 soybean plants were scored 14 days after inoculation.

The average of the percentage of the leaf area showing fungal colonies or strong yellowing/browning on all leaves was considered as diseased leaf area. At all 22 soybean T0 plants expressing ADR-1 (expression checked by RT-PCR) were evaluated in parallel to non-transgenic control plants. Clones from non-transgenic soy plants were used as control. The median of the diseased leaf area is shown in FIG. 7 for plants expressing recombinant ADR-1 compared with wild-type plants. Overexpression of ADR-1 strongly reduces the diseased leaf area in comparison to non-transgenic control plants. This data clearly indicate that the in planta expression of the ADR-1 expression vector construct lead to a lower disease scoring of transgenic plants compared to non-transgenic controls. So, the expression of ADR-1 in soy enhances the resistance of soy against soybean rust.

The invention claimed is:

1. A method for preventing, reducing, or delaying soybean rust infection in a soybean plant, the method comprising:

(1) providing a transgenic soybean plant comprising an exogenous nucleic acid encoding an Activated Disease Resistance 1 (ADR-1) protein having an amino acid sequence with at least 90% identity to SEQ ID NO: 2, wherein the ADR-1 protein confers increased resistance against soybean rust infection thereto in comparison to a wild type soybean plant, wherein the soybean rust is *Phakopsora paryhizi* and/or *Phakopsora meibomiae*; and (2) growing the transgenic soybean plant in the presence of a soybean rust, wherein soybean rust infection is prevented, reduced, or delayed in the transgenic soybean plant as compared to a wild type soybean plant.

2. The method according to claim 1, wherein the exogenous nucleic acid is in functional linkage with a promoter, and the promoter is a constitutive promoter, a pathogen-inducible promoter, or a mesophyll-specific promoter.

3. The method of claim 1, wherein the exogenous nucleic acid encodes an ADR-1 protein with at least 95% identity to SEQ ID NO: 2.

4. The method of claim 1, wherein the exogenous nucleic acid encodes an ADR-1 protein with at least 98% identity to SEQ ID NO: 2.

5. The method of claim 1, wherein the exogenous nucleic acid encodes an ADR-1 protein with 100% identity to SEQ ID NO: 2.

* * * * *

SEQUENCE LISTING

```
<160> NUMBER OF SEQ ID NOS: 11

<210> SEQ ID NO 1
<211> LENGTH: 2364
<212> TYPE: DNA
<213> ORGANISM: Arabidopsis thaliana

<400> SEQUENCE: 1
```

-continued

```
atggcttcgt tcatagatct tttcgccggc gacatcacga cgcaactctt aaagctgctc     60
gctctagtag ctaacacagt ctacagttgc aaaggaatcg ccgaacgact gatcacgatg    120
atcagagacg ttcaaccaac gatcagggag atccaataca gtggcgcgga gctgagtaac    180
catcaccaaa ctcaactggg agtattctat gagatcttgg agaaagcaag aaagctatgt    240
gaaaaggttt taagatgcaa taggtggaac cttaaacatg tgtaccacgc gaataagatg    300
aaggatctcg agaaacaaat atctcgtttc ctcaacagcc agattttgct ctttgttctt    360
gctgaggtat gtcatctacg ggtcaatggt gacaggattg agaggaatat ggatagactg    420
ttgactgagc ggaatgattc tttgtcgttt ccggagacta tgatggagat tgagacggta    480
agcgatccgg agattcagac ggtattggaa ttggggaaga aaaaggtgaa ggagatgatg    540
tttaagttta cggatacaca tttgtttggg atctctggaa tgagcggttc agggaaaacc    600
actcttgcaa tagagctttc aaaggacgat gatgttcgag gactctttaa gaataaggtt    660
ttgtttttga ctgtgtcacg gtctccgaat tttgagaatt tggagtcttg tatacgagaa    720
tttctttatg atggagttca tcaacggaag ctagtgattc ttgatgatgt ttggacaagg    780
gagtccttgg acaggctgat gtctaaaatt cgtggaagca ctactttagt agtgtcacgg    840
tccaagcttg cagatcctag aaccacctac aatgtggaat tattaaagaa agatgaagca    900
atgtctcttt tgtgtctctg tgctttcgaa caaaagtccc cgccttctcc attcaacaaa    960
tatttggtga agcaggttgt tgatgagtgt aaaggtttac ctttatcttt gaaagttctt   1020
ggtgcttcgt taaaaaacaa acctgaaaga tattgggaag gcgtagtgaa gaggttatta   1080
agaggagaag ctgctgatga aactcatgag agcagagtgt ttgctcatat ggaagaaagt   1140
ctagaaaacc tcgacccgaa aatccgagac tgtttcttgg atatgggtgc tttccctgaa   1200
gacaagaaga tccctcttga tcttctcacg agcgtgtggg ttgagaggca tgatattgac   1260
gaggaaactg cgttttcctt tgttcttcgt ttagctgaca agaatctcct tactatagtg   1320
aacaatccga ggtttggcga tgtgcacatt ggctactatg atgtatttgt gacgcaacac   1380
gatgttttga gagacctagc ccttcatatg tccaatcgtg tggacgtaaa taggagagag   1440
cggttattaa tgccaaaaac agagccagtg cttccaagag aatgggaaaa gaataaagat   1500
gagccatttg atgccaagat agtttccctt catacagggg aaatggatga aatgaattgg   1560
tttgacatgg acctccctaa ggcagaagtt ttaatactga acttctcttc ggacaactac   1620
gtcttgccac catttattgg taagatgagt agactcaggg tgctcgtgat tatcaacaat   1680
ggcatgtctc ctgcgcgtct acatggcttc tccatctttg ccaatttggc caaactgagg   1740
agtctctggc tcaagagggt acatgtccct gaactcacca gctgcaccat tccactgaaa   1800
aacctgcaca agatacatct aatcttttgt aaggtcaaga acagctttgt tcagacgtca   1860
ttcgacatct cgaaaatatt cccaagcttg tctgatctca ctattgatca ctgtgatgat   1920
cttttggaac taaaatccat atttggaata acctctctca actctctcag cataaccaac   1980
tgtccacgga ttcttgaatt gcccaagaat ttgagtaacg tacagtccct tgaacgtcta   2040
aggttatatg cctgccccga gctgatatcc ctcccggtcg aagtttgtga gctgccatgt   2100
ctaaagtacg ttgacatttc acagtgtgtc agcctggttt ctcttcctga aaagtttgga   2160
aagctaggga gtcttgagaa aattgacatg agagaatgca gtttattggg tttaccaagt   2220
tctgtagctg cacttgtgtc tctacgccat gtcatttgcg atgaggagac ttcgtctatg   2280
tgggaaatgg tcaagaaggt ggttcctgaa ctttgcattg aagtcgccaa aaaatgcttc   2340
```

accgtggatt ggcttgacga ttag 2364

<210> SEQ ID NO 2
<211> LENGTH: 787
<212> TYPE: PRT
<213> ORGANISM: Arabidopsis thaliana

<400> SEQUENCE: 2

```
Met Ala Ser Phe Ile Asp Leu Phe Ala Gly Asp Ile Thr Thr Gln Leu
1               5                   10                  15

Leu Lys Leu Leu Ala Leu Val Ala Asn Thr Val Tyr Ser Cys Lys Gly
            20                  25                  30

Ile Ala Glu Arg Leu Ile Thr Met Ile Arg Asp Val Gln Pro Thr Ile
        35                  40                  45

Arg Glu Ile Gln Tyr Ser Gly Ala Glu Leu Ser Asn His His Gln Thr
    50                  55                  60

Gln Leu Gly Val Phe Tyr Glu Ile Leu Glu Lys Ala Arg Lys Leu Cys
65                  70                  75                  80

Glu Lys Val Leu Arg Cys Asn Arg Trp Asn Leu Lys His Val Tyr His
                85                  90                  95

Ala Asn Lys Met Lys Asp Leu Glu Lys Gln Ile Ser Arg Phe Leu Asn
            100                 105                 110

Ser Gln Ile Leu Leu Phe Val Leu Ala Glu Val Cys His Leu Arg Val
        115                 120                 125

Asn Gly Asp Arg Ile Glu Arg Asn Met Asp Arg Leu Leu Thr Glu Arg
    130                 135                 140

Asn Asp Ser Leu Ser Phe Pro Glu Thr Met Met Glu Ile Glu Thr Val
145                 150                 155                 160

Ser Asp Pro Glu Ile Gln Thr Val Leu Glu Leu Gly Lys Lys Lys Val
                165                 170                 175

Lys Glu Met Met Phe Lys Phe Thr Asp Thr His Leu Phe Gly Ile Ser
            180                 185                 190

Gly Met Ser Gly Ser Gly Lys Thr Thr Leu Ala Ile Glu Leu Ser Lys
        195                 200                 205

Asp Asp Asp Val Arg Gly Leu Phe Lys Asn Lys Val Leu Phe Leu Thr
    210                 215                 220

Val Ser Arg Ser Pro Asn Phe Glu Asn Leu Glu Ser Cys Ile Arg Glu
225                 230                 235                 240

Phe Leu Tyr Asp Gly Val His Gln Arg Lys Leu Val Ile Leu Asp Asp
                245                 250                 255

Val Trp Thr Arg Glu Ser Leu Asp Arg Leu Met Ser Lys Ile Arg Gly
            260                 265                 270

Ser Thr Thr Leu Val Val Ser Arg Ser Lys Leu Ala Asp Pro Arg Thr
        275                 280                 285

Thr Tyr Asn Val Glu Leu Leu Lys Lys Asp Glu Ala Met Ser Leu Leu
    290                 295                 300

Cys Leu Cys Ala Phe Glu Gln Lys Ser Pro Pro Ser Pro Phe Asn Lys
305                 310                 315                 320

Tyr Leu Val Lys Gln Val Val Asp Glu Cys Lys Gly Leu Pro Leu Ser
                325                 330                 335

Leu Lys Val Leu Gly Ala Ser Leu Lys Asn Lys Pro Glu Arg Tyr Trp
            340                 345                 350

Glu Gly Val Val Lys Arg Leu Leu Arg Gly Glu Ala Ala Asp Glu Thr
        355                 360                 365
```

```
His Glu Ser Arg Val Phe Ala His Met Glu Glu Ser Leu Glu Asn Leu
    370                 375                 380

Asp Pro Lys Ile Arg Asp Cys Phe Leu Asp Met Gly Ala Phe Pro Glu
385                 390                 395                 400

Asp Lys Lys Ile Pro Leu Asp Leu Leu Thr Ser Val Trp Val Glu Arg
                405                 410                 415

His Asp Ile Asp Glu Glu Thr Ala Phe Ser Phe Val Leu Arg Leu Ala
            420                 425                 430

Asp Lys Asn Leu Leu Thr Ile Val Asn Asn Pro Arg Phe Gly Asp Val
        435                 440                 445

His Ile Gly Tyr Tyr Asp Val Phe Val Thr Gln His Asp Val Leu Arg
    450                 455                 460

Asp Leu Ala Leu His Met Ser Asn Arg Val Asp Val Asn Arg Arg Glu
465                 470                 475                 480

Arg Leu Leu Met Pro Lys Thr Glu Pro Val Leu Pro Arg Glu Trp Glu
                485                 490                 495

Lys Asn Lys Asp Glu Pro Phe Asp Ala Lys Ile Val Ser Leu His Thr
            500                 505                 510

Gly Glu Met Asp Glu Met Asn Trp Phe Asp Met Asp Leu Pro Lys Ala
        515                 520                 525

Glu Val Leu Ile Leu Asn Phe Ser Ser Asp Asn Tyr Val Leu Pro Pro
    530                 535                 540

Phe Ile Gly Lys Met Ser Arg Leu Arg Val Leu Val Ile Ile Asn Asn
545                 550                 555                 560

Gly Met Ser Pro Ala Arg Leu His Gly Phe Ser Ile Phe Ala Asn Leu
                565                 570                 575

Ala Lys Leu Arg Ser Leu Trp Leu Lys Arg Val His Val Pro Glu Leu
            580                 585                 590

Thr Ser Cys Thr Ile Pro Leu Lys Asn Leu His Lys Ile His Leu Ile
        595                 600                 605

Phe Cys Lys Val Lys Asn Ser Phe Val Gln Thr Ser Phe Asp Ile Ser
    610                 615                 620

Lys Ile Phe Pro Ser Leu Ser Asp Leu Thr Ile Asp His Cys Asp Asp
625                 630                 635                 640

Leu Leu Glu Leu Lys Ser Ile Phe Gly Ile Thr Ser Leu Asn Ser Leu
                645                 650                 655

Ser Ile Thr Asn Cys Pro Arg Ile Leu Glu Leu Pro Lys Asn Leu Ser
            660                 665                 670

Asn Val Gln Ser Leu Glu Arg Leu Arg Leu Tyr Ala Cys Pro Glu Leu
        675                 680                 685

Ile Ser Leu Pro Val Glu Val Cys Glu Leu Pro Cys Leu Lys Tyr Val
    690                 695                 700

Asp Ile Ser Gln Cys Val Ser Leu Val Ser Leu Pro Glu Lys Phe Gly
705                 710                 715                 720

Lys Leu Gly Ser Leu Glu Lys Ile Asp Met Arg Glu Cys Ser Leu Leu
                725                 730                 735

Gly Leu Pro Ser Ser Val Ala Ala Leu Val Ser Leu Arg His Val Ile
            740                 745                 750

Cys Asp Glu Glu Thr Ser Ser Met Trp Glu Met Val Lys Lys Val Val
        755                 760                 765

Pro Glu Leu Cys Ile Glu Val Ala Lys Lys Cys Phe Thr Val Asp Trp
    770                 775                 780

Leu Asp Asp
```

-continued

785

<210> SEQ ID NO 3
<211> LENGTH: 51
<212> TYPE: DNA
<213> ORGANISM: Arabidopsis thaliana

<400> SEQUENCE: 3
cacgcgaata agatgaagga tctcgagaaa caaatatctc gtttcctcaa c 51

<210> SEQ ID NO 4
<211> LENGTH: 17
<212> TYPE: PRT
<213> ORGANISM: Arabidopsis thaliana

<400> SEQUENCE: 4

His Ala Asn Lys Met Lys Asp Leu Glu Lys Gln Ile Ser Arg Phe Leu
1 5 10 15

Asn

<210> SEQ ID NO 5
<211> LENGTH: 825
<212> TYPE: DNA
<213> ORGANISM: Arabidopsis thaliana

<400> SEQUENCE: 5
ttgtttggga tctctggaat gagcggttca gggaaaacca ctcttgcaat agagctttca 60
aaggacgatg atgttcgagg actctttaag aataaggttt tgtttttgac tgtgtcacgg 120
tctccgaatt ttgagaattt ggagtcttgt atacgagaat ttctttatga tggagttcat 180
caacggaagc tagtgattct tgatgatgtt tggacaaggg agtccttgga caggctgatg 240
tctaaaattc gtggaagcac tactttagta gtgtcacggt ccaagcttgc agatcctaga 300
accacctaca atgtggaatt attaaagaaa gatgaagcaa tgtctctttt gtgtctctgt 360
gctttcgaac aaaagtcccc gccttctcca ttcaacaaat atttggtgaa gcaggttgtt 420
gatgagtgta aaggtttacc tttatctttg aaagttcttg gtgcttcgtt aaaaaacaaa 480
cctgaaagat attgggaagg cgtagtgaag aggttattaa gaggagaagc tgctgatgaa 540
actcatgaga gcagagtgtt tgctcatatg gaagaaagtc tagaaaacct cgacccgaaa 600
atccgagact gtttcttgga tatgggtgct ttccctgaag acaagaagat ccctcttgat 660
cttctcacga gcgtgtgggt tgagaggcat gatattgacg aggaaactgc gttttccttt 720
gttcttcgtt tagctgacaa gaatctcctt actatagtga acaatccgag gtttggcgat 780
gtgcacattg gctactatga tgtatttgtg acgcaacacg atgtt 825

<210> SEQ ID NO 6
<211> LENGTH: 275
<212> TYPE: PRT
<213> ORGANISM: Arabidopsis thaliana

<400> SEQUENCE: 6

Leu Phe Gly Ile Ser Gly Met Ser Gly Ser Gly Lys Thr Thr Leu Ala
1 5 10 15

Ile Glu Leu Ser Lys Asp Asp Asp Val Arg Gly Leu Phe Lys Asn Lys
20 25 30

Val Leu Phe Leu Thr Val Ser Arg Ser Pro Asn Phe Glu Asn Leu Glu
35 40 45

Ser Cys Ile Arg Glu Phe Leu Tyr Asp Gly Val His Gln Arg Lys Leu

-continued

```
    50                  55                  60

Val Ile Leu Asp Asp Val Trp Thr Arg Glu Ser Leu Asp Arg Leu Met
65                  70                  75                  80

Ser Lys Ile Arg Gly Ser Thr Thr Leu Val Val Ser Arg Ser Lys Leu
                85                  90                  95

Ala Asp Pro Arg Thr Thr Tyr Asn Val Glu Leu Leu Lys Lys Asp Glu
            100                 105                 110

Ala Met Ser Leu Leu Cys Leu Cys Ala Phe Glu Gln Lys Ser Pro Pro
        115                 120                 125

Ser Pro Phe Asn Lys Tyr Leu Val Lys Gln Val Val Asp Glu Cys Lys
    130                 135                 140

Gly Leu Pro Leu Ser Leu Lys Val Leu Gly Ala Ser Leu Lys Asn Lys
145                 150                 155                 160

Pro Glu Arg Tyr Trp Glu Gly Val Val Lys Arg Leu Leu Arg Gly Glu
                165                 170                 175

Ala Ala Asp Glu Thr His Glu Ser Arg Val Phe Ala His Met Glu Glu
            180                 185                 190

Ser Leu Glu Asn Leu Asp Pro Lys Ile Arg Asp Cys Phe Leu Asp Met
        195                 200                 205

Gly Ala Phe Pro Glu Asp Lys Lys Ile Pro Leu Asp Leu Leu Thr Ser
    210                 215                 220

Val Trp Val Glu Arg His Asp Ile Asp Glu Glu Thr Ala Phe Ser Phe
225                 230                 235                 240

Val Leu Arg Leu Ala Asp Lys Asn Leu Leu Thr Ile Val Asn Asn Pro
                245                 250                 255

Arg Phe Gly Asp Val His Ile Gly Tyr Tyr Asp Val Phe Val Thr Gln
            260                 265                 270

His Asp Val
        275


<210> SEQ ID NO 7
<211> LENGTH: 822
<212> TYPE: DNA
<213> ORGANISM: Arabidopsis thaliana

<400> SEQUENCE: 7

ttgagagacc tagcccttca tatgtccaat cgtgtggacg taaataggag agagcggtta      60

ttaatgccaa aaacagagcc agtgcttcca agagaatggg aaaagaataa agatgagcca     120

tttgatgcca agatagtttc ccttcataca ggggaaatgg atgaaatgaa ttggtttgac     180

atggacctcc ctaaggcaga agttttaata ctgaacttct cttcggacaa ctacgtcttg     240

ccaccattta ttggtaagat gagtagactc agggtgctcg tgattatcaa caatggcatg     300

tctcctgcgc gtctacatgg cttctccatc tttgccaatt tggccaaact gaggagtctc     360

tggctcaaga gggtacatgt ccctgaactc accagctgca ccattccact gaaaaacctg     420

cacaagatac atctaatctt ttgtaaggtc aagaacagct ttgttcagac gtcattcgac     480

atctcgaaaa tattcccaag cttgtctgat ctcactattg atcactgtga tgatcttttg     540

gaactaaaat ccatatttgg aataacctct ctcaactctc tcagcataac caactgtcca     600

cggattcttg aattgcccaa gaatttgagt aacgtacagt cccttgaacg tctaaggtta     660

tatgcctgcc ccgagctgat atccctcccg gtcgaagttt gtgagctgcc atgtctaaag     720

tacgttgaca tttcacagtg tgtcagcctg gtttctcttc ctgaaaagtt tggaaagcta     780

gggagtcttg agaaaattga catgagagaa tgcagtttat tg                        822
```

<210> SEQ ID NO 8
<211> LENGTH: 274
<212> TYPE: PRT
<213> ORGANISM: Arabidopsis thaliana

<400> SEQUENCE: 8

```
Leu Arg Asp Leu Ala Leu His Met Ser Asn Arg Val Asp Val Asn Arg
1               5                   10                  15

Arg Glu Arg Leu Leu Met Pro Lys Thr Glu Pro Val Leu Pro Arg Glu
            20                  25                  30

Trp Glu Lys Asn Lys Asp Glu Pro Phe Asp Ala Lys Ile Val Ser Leu
        35                  40                  45

His Thr Gly Glu Met Asp Glu Met Asn Trp Phe Asp Met Asp Leu Pro
    50                  55                  60

Lys Ala Glu Val Leu Ile Leu Asn Phe Ser Ser Asp Asn Tyr Val Leu
65                  70                  75                  80

Pro Pro Phe Ile Gly Lys Met Ser Arg Leu Arg Val Leu Val Ile Ile
                85                  90                  95

Asn Asn Gly Met Ser Pro Ala Arg Leu His Gly Phe Ser Ile Phe Ala
            100                 105                 110

Asn Leu Ala Lys Leu Arg Ser Leu Trp Leu Lys Arg Val His Val Pro
        115                 120                 125

Glu Leu Thr Ser Cys Thr Ile Pro Leu Lys Asn Leu His Lys Ile His
    130                 135                 140

Leu Ile Phe Cys Lys Val Lys Asn Ser Phe Val Gln Thr Ser Phe Asp
145                 150                 155                 160

Ile Ser Lys Ile Phe Pro Ser Leu Ser Asp Leu Thr Ile Asp His Cys
                165                 170                 175

Asp Asp Leu Leu Glu Leu Lys Ser Ile Phe Gly Ile Thr Ser Leu Asn
            180                 185                 190

Ser Leu Ser Ile Thr Asn Cys Pro Arg Ile Leu Glu Leu Pro Lys Asn
        195                 200                 205

Leu Ser Asn Val Gln Ser Leu Glu Arg Leu Arg Leu Tyr Ala Cys Pro
    210                 215                 220

Glu Leu Ile Ser Leu Pro Val Glu Val Cys Glu Leu Pro Cys Leu Lys
225                 230                 235                 240

Tyr Val Asp Ile Ser Gln Cys Val Ser Leu Val Ser Leu Pro Glu Lys
                245                 250                 255

Phe Gly Lys Leu Gly Ser Leu Glu Lys Ile Asp Met Arg Glu Cys Ser
            260                 265                 270

Leu Leu
```

<210> SEQ ID NO 9
<211> LENGTH: 13666
<212> TYPE: DNA
<213> ORGANISM: Artificial sequence
<220> FEATURE:
<223> OTHER INFORMATION: vector

<400> SEQUENCE: 9

```
gtgattttgt gccgagctgc cggtcgggga gctgttggct ggctggtggc aggatatatt      60

gtggtgtaaa caaattgacg cttagacaac ttaataacac attgcggacg tctttaatgt     120

actgaattaa catccgtttg atacttgtct aaaattggct gatttcgagt gcatctatgc     180

ataaaaacaa tctaatgaca attattacca agcagagctt gacaggaggc ccgatctagt     240
```

-continued

```
aacatagatg acaccgcgcg cgataattta tcctagtttg cgcgctatat tttgttttct    300
atcgcgtatt aaatgtataa ttgcgggact ctaatcataa aaacccatct cataaataac    360
gtcatgcatt acatgttaat tattacatgc ttaacgtaat tcaacagaaa ttatatgata    420
atcatcgcaa gaccggcaac aggattcaat cttaagaaac tttattgcca aatgtttgaa    480
cgatcgggga tcatccgggt ctgtggcggg aactccacga aaatatccga acgcagcaag    540
atctagagct tgggtcggga aattaccctg ttatccctat cagtatttaa tccggccatc    600
tccttccgtt atgacatcgt tgaaagtgcc accattcggg atcatcggca acacatgttc    660
ttggtgcgga caaatcacat ccaacaggta aggtcctggt gtatccagca ttgtctgaat    720
agcttctcgg agatctgctt tctttgtcac cctcgccgct ggaatcccgc aagctgctgc    780
aaacagcaac atgttcggga atatctcgtc ctcctgagcc ggatccccga gaaatgtgtg    840
agctcggtta gctttgtaga accgatcttc ccattgcata accatgccaa gatgctggtt    900
gtttaataaa agtaccttca ctggaagatt ctctacacga atagtggcta gctcttgcac    960
attcattata aagcttccat ctccgtcaat atccacaact atcgcatcag ggttagcaac   1020
agacgctcca atcgcagcag gaagtccaaa tcccatagct ccaaggcctc ctgatgatag   1080
ccactgcctt ggtttcttgt aattgtagaa ctgcgccgcc cacatttgat gttgcccgac   1140
accagtactt attatggctt ttccatcagt caactcatca aggaccttaa tcgcatactg   1200
tggaggaata gcttccccaa acgtcttaaa gctcaacgga aacttctgtt tctgtacgtt   1260
caactcattc ctccaaactc caaaatcaag cttaagctcc tccgctcggt tctcaagaac   1320
cttattcatc ccttgcaaag ccagcttaac atcaccacac acagacacat gaggagtctt   1380
attcttccca atctcagccg agtcaatatc aatatgaaca atcttagccc tactagcaaa   1440
agcctcaagc ttacccgtga cacgatcatc aaaccttacc ccaaacgcca acaacaaatc   1500
actatgctcc acagcgtaat ttgcatacac agtcccatgc attccaagca tatgtaacga   1560
caactcatca tcacaaggat aagatcccag ccccatcaac gtactcgcaa cagggatccc   1620
cgtaagctca acaaacctac ccaattcatc gctagaattc aaacaaccac caccaacata   1680
caacacaggc ttcttagact cagaaatcaa cctaacaatc tgctccaaat gagaatcttc   1740
cggaggttta ggcatcctag acatataacc aggtaatctc atagcctgtt cccaattagg   1800
aatcgcaagc tgttgttgaa tatctttagg aacatcaacc aaaacaggtc caggtctacc   1860
agaagtagct aaaaagaaag cttcctcaat aatcctaggg atatcttcaa catccatcac   1920
aagatagtta tgcttcgtaa tcgaacgcgt tacctcaaca atcggagtct cttgaaacgc   1980
atctgtacca atcatacgac gagggacttg tcctgtgatt gctacaagag gaacactatc   2040
taacaacgca tcggctaatc cgctaacgag atttgtagct ccgggacctg aagtggctat   2100
acagatacct ggtttacctg aggatcgagc gtatccttct gctgcgaata cacctccttg   2160
ttcgtgacga ggaaggacgt tacggattga ggaagagcgg gttaaggctt ggtgaatctc   2220
cattgatgta cctccagggt aagcgaatac ggtttctacg ccttgacgtt ctaaagcttc   2280
gacgaggata tcagcgcctt tgcggggttg atctggagcg aatcgggaga tgaatgtttc   2340
gggtttggta ggtttggttg gagagggagt ggttgtgaca ttggtggttg tgttgagcac   2400
ggcggagatg gaggagggag agctggattt gataccgcgg cggcgggagg aggaggatga   2460
tttgttgggg tttagggaga atgggaggga gaatctggag attggtaatg gtgatttgga   2520
ggaggaagga gatggtttgg tggagaagga gatcgaagaa gatgttgttg ttgttgttgt   2580
```

-continued

```
tgccgccgcc atggttcagc tgcacataca taacatatca agatcagaac acacatatac   2640
acacacaaat acaatcaagt caacaactcc aaaaagtcca gatctacata tatacatacg   2700
taaataacaa aatcatgtaa ataatcacaa tcatgtaatc cagatctatg cacatatata   2760
tatacacaat taataaaaaa aatgatataa cagatctata tctatgtatg taacaacaca   2820
atcagatgag agaagtgatg ttttcagatc tgtatacata caaacacaaa cagatgaaca   2880
attgatacgt agatccatat gtatacgtac aattagctac acgattaaat gaaaaaaatc   2940
aacgatttcg gattggtaca cacaaacgca acaatatgaa gaaattcata tctgattaga   3000
tataaacata accacgtgta gatacacagt caaatcaaca aatttatagc ttctaaacgg   3060
atgagatgaa caagataaag atattcacat aaggcataca taagataagc agattaacaa   3120
actagcaata atacatacct aattaaaaca aggaataaca gagagagaga gagagagaga   3180
gatttacctt gaaaatgaag aggagaagag aggatttctt aaaattgggg gtagagaaag   3240
aaagatgatg aattgtgaga aaggagagat agaagggggg gttgtatata taggctgtag   3300
aagattattt ttgtgtttga ggcggtgaag gaagagggga tctgactatg acacgtttgc   3360
ggttacgtat ttcgatagga gtctttcaac gcttaacgcc gttactctat atgaccgttt   3420
gggccgtaac ggggccgttt gttaacgctg atgttgattc ttttctttct ttctttcttc   3480
ctttttttaaa gaagcaattg tacaatcgtt gctagctgtc aaacggataa ttcggatacg   3540
gatatgccta tattcatatc cgtaattttt ggattcgaat tttcccctct agggataaca   3600
gggtaatgcc cgatctagta acatagatga caccgcgcgc gataatttat cctagtttgc   3660
gcgctatatt ttgttttcta tcgcgtatta aatgtataat tgcgggactc taatcataaa   3720
aacccatctc ataaataacg tcatgcatta catgttaatt attacatgct taacgtaatt   3780
caacagaaat tatatgataa tcatcgcaag accggcaaca ggattcaatc ttaagaaact   3840
ttattgccaa atgtttgaac gatggtacct cgagcggccg ccagtgtgat ggatatctgc   3900
agaattcgcc cttaaaaaag atatccggcc agtgaattat caactatgta taataaagtt   3960
gggtaccccc gatccccccc actccgccct acactcgtat atatatgcct aaacctgccc   4020
cgttcctcat atgtgatatt attatttcat tattaggtat aagatagtaa acgataagga   4080
aagacaattt attgagaaag ccatgctaaa atatagatag atatacctta gcaggtgttt   4140
attttacaac ataacataac atagtagcta gccagcaggc aggctaaaac atagtatagt   4200
ctatctgcag gggtacggt cgaggcggcc ttaattaatc gatagggga agcttggcgt   4260
aatcatggcc actttgtaca agaaagctgg gtccatgatt acgccaagct tgcatgccca   4320
tatgctcgag gcggccgcgg cgcgccaatt gactagtagg cctatcgatt aattaaggcc   4380
gcagatatca gatctggtcg acctaatcgt caagccaatc cacggtgaag cattttttgg   4440
cgacttcaat gcaaagttca ggaaccacct tcttgaccat ttcccacata gacgaagtct   4500
cctcatcgca aatgacatgg cgtagagaca caagtgcagc tacagaactt ggtaaaccca   4560
ataaactgca ttctctcatg tcaattttct caagactccc tagctttcca aacttttcag   4620
gaagagaaac caggctgaca cactgtgaaa tgtcaacgta ctttagacat ggcagctcac   4680
aaacttcgac cgggagggat atcagctcgg ggcaggcata taaccttaga cgttcaaggg   4740
actgtacgtt actcaaattc ttgggcaatt caagaatccg tggacagttg gttatgctga   4800
gagagttgag agaggttatt ccaaatatgg attttagttc caaaagatca tcacagtgat   4860
caatagtgag atcagacaag cttgggaata ttttcgagat gtcgaatgac gtctgaacaa   4920
agctgttctt gaccttacaa aagattagat gtatcttgtg caggtttttc agtggaatgg   4980
```

-continued

```
tgcagctggt gagttcaggg acatgtaccc tcttgagcca gagactcctc agtttggcca   5040
aattggcaaa gatggagaag ccatgtagac gcgcaggaga catgccattg ttgataatca   5100
cgagcaccct gagtctactc atcttaccaa taaatggtgg caagacgtag ttgtccgaag   5160
agaagttcag tattaaaact tctgccttag ggaggtccat gtcaaaccaa ttcatttcat   5220
ccatttcccc tgtatgaagg gaaactatct tggcatcaaa tggctcatct ttattctttt   5280
cccattctct tggaagcact ggctctgttt ttggcattaa taaccgctct ctcctattta   5340
cgtccacacg attggacata tgaagggcta ggtctctcaa aacatcgtgt tgcgtcacaa   5400
atacatcata gtagccaatg tgcacatcgc caaacctcgg attgttcact atagtaagga   5460
gattcttgtc agctaaacga agaacaaagg aaaacgcagt ttcctcgtca atatcatgcc   5520
tctcaaccca cacgctcgtg agaagatcaa gagggatctt cttgtcttca gggaaagcac   5580
ccatatccaa gaaacagtct cggattttcg ggtcgaggtt ttctagactt tcttccatat   5640
gagcaaacac tctgctctca tgagtttcat cagcagcttc tcctcttaat aacctcttca   5700
ctacgccttc ccaatatctt tcaggtttgt tttttaacga agcaccaaga actttcaaag   5760
ataaaggtaa acctttacac tcatcaacaa cctgcttcac caaatatttg ttgaatggag   5820
aaggcgggga cttttgttcg aaagcacaga gacacaaaag agacattgct tcatctttct   5880
ttaataattc cacattgtag gtggttctag gatctgcaag cttggaccgt gacactacta   5940
aagtagtgct tccacgaatt ttagacatca gcctgtccaa ggactccctt gtccaaacat   6000
catcaagaat cactagcttc cgttgatgaa ctccatcata aagaaattct cgtatacaag   6060
actccaaatt ctcaaaattc ggagaccgtg acacagtcaa aaacaaaacc ttattcttaa   6120
agagtcctcg aacatcatcg tcctttgaaa gctctattgc aagagtggtt ttccctgaac   6180
cgctcattcc agagatccca aacaaatgtg tatccgtaaa cttaaacatc atctccttca   6240
ccttttcttt ccccaattcc aataccgtct gaatctccgg atcgcttacc gtctcaatct   6300
ccatcatagt ctccggaaac gacaaagaat cattccgctc agtcaacagt ctatccatat   6360
tcctctcaat cctgtcacca ttgacccgta gatgacatac ctcagcaaga acaaagagca   6420
aaatctggct gttgaggaaa cgagatattt gtttctcgag atccttcatc ttattcgcgt   6480
ggtacacatg tttaaggttc cacctattgc atcttaaaac cttttcacat agctttcttg   6540
ctttctccaa gatctcatag aatactccca gttgagtttg gtgatggtta ctcagctccg   6600
cgccactgta ttggatctcc ctgatcgttg gttgaacgtc tctgatcatc gtgatcagtc   6660
gttcggcgat tcctttgcaa ctgtagactg tgttagctac tagagcgagc agctttaaga   6720
gttgcgtcgt gatgtcgccg gcgaaaagat ctatgaacga agccatggta ccagcctgct   6780
tttttgtaca aacttgggta cggccgcaga tgggctgcac atacataaca tatcaagatc   6840
agaacacaca tatacacaca caaatacaat caagtcaaca actccaaaaa gtccagatct   6900
acatatatac atacgtaaat aacaaaatca tgtaaataat cacaatcatg taatccagat   6960
ctatgcacat atatatatac acaattaata aaaaaaatga tataacagat ctatatctat   7020
gtatgtaaca acacaatcag atgagagaag tgatgttttc agatctgtat acatacaaac   7080
acaaacagat gaacaattga tacgtagatc catatgtata cgtacaatta gctacacgat   7140
taaatgaaaa aaatcaacga tttcggattg gtacacacaa acgcaacaat atgaagaaat   7200
tcatatctga ttagatataa acataaccac gtgtagatac acagtcaaat caacaaattt   7260
atagcttcta aacggatgag atgaacaaga taaagatatt cacataaggc atacataaga   7320
```

-continued

```
taagcagatt aacaaactag caataataca tacctaatta aaacaaggaa taacagagag   7380
agagagagag agagagattt accttgaaaa tgaagaggag aagagaggat ttcttaaaat   7440
tgggggtaga gaaagaaaga tgatgaattg tgagaaagga gagatagaag ggggggttgt   7500
atatataggc tgtagaagat tatttttgtg tttgaggcgg tgaaggaaga ggggatctga   7560
ctatgacacg tttgcggtta cgtatttcga taggagtctt tcaacgctta acgccgttac   7620
tctatatgac cgtttgggcc gtaacggggc cgtttgttaa cgctgatgtt gattcttttc   7680
tttctttctt tcttcctttt ttaaagaagc aattgtacaa tcgttgctag ctgtcaaacg   7740
gataattcgg atacggatat gcctatattc atatccgtaa tttttggatt cgaattctag   7800
aggatccgcc caaagcttgg cgtaatcatg gcaacttttc tatacaaagt tgatagcttg   7860
gcgtaatcga tatctttttt aagggcgaat tccagcacac tggcggccgt tactagtacg   7920
gtacgattta aataagcttg gcgtaatcat ggtcatagct gtttcctact agatctgatt   7980
gtcgtttccc gccttcagtt taaactatca gtgtttgaca ggatatattg gcgggtaaac   8040
ctaagagaaa agagcgttta ttagaataat cggatattta aaagggcgtg aaaaggttta   8100
tccgttcgtc catttgtatg tccatggaac gcagtggcgg ttttcatggc ttgttatgac   8160
tgtttttttg gggtacagtc tatgcctcgg gcatccaagc agcaagcgcg ttacgccgtg   8220
ggtcgatgtt tgatgttatg gagcagcaac gatgttacgc agcagggcag tcgccctaaa   8280
acaaagttaa acatcatggg ggaagcggtg atcgccgaag tatcgactca actatcagag   8340
gtagttggcg tcatcgagcg ccatctcgaa ccgacgttgc tggccgtaca tttgtacggc   8400
tccgcagtgg atggcggcct gaagccacac agtgatattg atttgctggt tacggtgacc   8460
gtaaggcttg atgaaacaac gcggcgagct ttgatcaacg accttttgga aacttcggct   8520
tcccctggag agagcgagat tctccgcgct gtagaagtca ccattgttgt gcacgacgac   8580
atcattccgt ggcgttatcc agctaagcgc gaactgcaat ttggagaatg gcagcgcaat   8640
gacattcttg caggtatctt cgagccagcc acgatcgaca ttgatctggc tatcttgctg   8700
acaaaagcaa gagaacatag cgttgccttg gtaggtccag cggcggagga actctttgat   8760
ccggttcctg aacaggatct atttgaggcg ctaaatgaaa ccttaacgct atggaactcg   8820
ccgcccgact gggctggcga tgagcgaaat gtagtgctta cgttgtcccg catttggtac   8880
agcgcagtaa ccggcaaaat cgcgccgaag gatgtcgctg ccgactgggc aatggagcgc   8940
ctgccggccc agtatcagcc cgtcatactt gaagctagac aggcttatct tggacaagaa   9000
gaagatcgct tggcctcgcg cgcagatcag ttggaagaat ttgtccacta cgtgaaaggc   9060
gagatcacca aggtagtcgg caaataatgt ctagctagaa attcgttcaa gccgacgccg   9120
cttcgcggcg cggcttaact caagcgttag atgcactaag cacataattg ctcacagcca   9180
aactatcagg tcaagtctgc ttttattatt tttaagcgtg cataataagc cctacacaaa   9240
ttgggagata tatcatgcat gaccaaaatc ccttaacgtg agttttcgtt ccactgagcg   9300
tcagaccccg tagaaaagat caaaggatct tcttgagatc ctttttttct gcgcgtaatc   9360
tgctgcttgc aaacaaaaaa accaccgcta ccagcggtgg tttgtttgcc ggatcaagag   9420
ctaccaactc tttttccgaa ggtaactggc ttcagcagag cgcagatacc aaatactgtc   9480
cttctagtgt agccgtagtt aggccaccac ttcaagaact ctgtagcacc gcctacatac   9540
ctcgctctgc taatcctgtt accagtggct gctgccagtg gcgataagtc gtgtcttacc   9600
gggttggact caagacgata gttaccggat aaggcgcagc ggtcgggctg aacggggggt   9660
tcgtgcacac agcccagctt ggagcgaacg acctacaccg aactgagata cctacagcgt   9720
```

gagctatgag aaagcgccac gcttcccgaa gggagaaagg cggacaggta tccggtaagc 9780
ggcagggtcg gaacaggaga gcgcacgagg gagcttccag ggggaaacgc ctggtatctt 9840
tatagtcctg tcgggtttcg ccacctctga cttgagcgtc gatttttgtg atgctcgtca 9900 gggggcgga gcctatggaa aaacgccagc aacgcggcct ttttacggtt cctggccttt 9960
tgctggcctt ttgctcacat gttctttcct gcgttatccc ctgattctgt ggataaccgt 10020
attaccgcct ttgagtgagc tgataccgct cgccgcagcc gaacgaccga gcgcagcgag 10080
tcagtgagcg aggaagcgga agagcgcctg atgcggtatt ttctccttac gcatctgtgc 10140
ggtatttcac accgcatatg gtgcactctc agtacaatct gctctgatgc cgcatagtta 10200
agccagtata cactccgcta tcgctacgtg actgggtcat ggctgcgccc cgacacccgc 10260
caacacccgc tgacgcgccc tgacgggctt gtctgctccc ggcatccgct tacagacaag 10320
ctgtgaccgt ctccgggagc tgcatgtgtc agaggttttc accgtcatca ccgaaacgcg 10380
cgaggcaggg tgccttgatg tgggcgccgg cggtcgagtg gcgacggcgc ggcttgtccg 10440
cgccctggta gattgcctgg ccgtaggcca gccatttttg agcggccagc ggccgcgata 10500
ggccgacgcg aagcggcggg gcgtagggag cgcagcgacc gaagggtagg cgctttttgc 10560
agctcttcgg ctgtgcgctg gccagacagt tatgcacagg ccaggcgggt tttaagagtt 10620
ttaataagtt ttaaagagtt ttaggcggaa aaatcgcctt ttttctcttt tatatcagtc 10680
acttacatgt gtgaccggtt cccaatgtac ggctttgggt tcccaatgta cgggttccgg 10740
ttcccaatgt acggctttgg gttcccaatg tacgtgctat ccacaggaaa gagacctttt 10800
cgaccttttt cccctgctag ggcaatttgc cctagcatct gctccgtaca ttaggaaccg 10860
gcggatgctt cgccctcgat caggttgcgg tagcgcatga ctaggatcgg gccagcctgc 10920
cccgcctcct ccttcaaatc gtactccggc aggtcatttg acccgatcag cttgcgcacg 10980
gtgaaacaga acttcttgaa ctctccggcg ctgccactgc gttcgtagat cgtcttgaac 11040
aaccatctgg cttctgcctt gcctgcggcg cggcgtgcca ggcggtagag aaaacggccg 11100
atgccgggat cgatcaaaaa gtaatcgggg tgaaccgtca gcacgtccgg gttcttgcct 11160
tctgtgatct cgcggtacat ccaatcagct agctcgatct cgatgtactc cggccgcccg 11220
gtttcgctct ttacgatctt gtagcggcta atcaaggctt caccctcgga taccgtcacc 11280
aggcggccgt tcttggcctt cttcgtacgc tgcatggcaa cgtgcgtggt gtttaaccga 11340
atgcaggttt ctaccaggtc gtctttctgc tttccgccat cggctcgccg gcagaacttg 11400
agtacgtccg caacgtgtgg acggaacacg cggccgggct tgtctccctt cccttcccgg 11460
tatcggttca tggattcggt tagatgggaa accgccatca gtaccaggtc gtaatcccac 11520
acactggcca tgccggccgg ccctgcggaa acctctacgt gcccgtctgg aagctcgtag 11580
cggatcacct cgccagctcg tcggtcacgc ttcgacagac ggaaaacggc cacgtccatg 11640
atgctgcgac tatcgcgggt gcccacgtca tagagcatcg gaacgaaaaa atctggttgc 11700
tcgtcgccct tgggcggctt cctaatcgac ggcgcaccgg ctgccggcgg ttgccgggat 11760
tctttgcgga ttcgatcagc ggccgcttgc cacgattcac cggggcgtgc ttctgcctcg 11820
atgcgttgcc gctgggcggc ctgcgcggcc ttcaacttct ccaccaggtc atcacccagc 11880
gccgcgccga tttgtaccgg gccggatggt ttgcgaccgc tcacgccgat tcctcgggct 11940
tgggggttcc agtgccattg cagggccggc agacaaccca gccgcttacg cctggccaac 12000
cgcccgttcc tccacacatg ggcattcca cggcgtcggt gcctggttgt tcttgatttt 12060

-continued

```
ccatgccgcc tcctttagcc gctaaaattc atctactcat ttattcattt gctcatttac  12120
tctggtagct gcgcgatgta ttcagatagc agctcggtaa tggtcttgcc ttggcgtacc  12180
gcgtacatct tcagcttggt gtgatcctcc gccggcaact gaaagttgac ccgcttcatg  12240
gctggcgtgt ctgccaggct ggccaacgtt gcagccttgc tgctgcgtgc gctcggacgg  12300
ccggcactta gcgtgtttgt gcttttgctc attttctctt tacctcatta actcaaatga  12360
gttttgattt aatttcagcg gccagcgcct ggacctcgcg ggcagcgtcg ccctcgggtt  12420
ctgattcaag aacggttgtg ccggcggcgg cagtgcctgg gtagctcacg cgctgcgtga  12480
tacgggactc aagaatgggc agctcgtacc cggccagcgc ctcggcaacc tcaccgccga  12540
tgcgcgtgcc tttgatcgcc cgcgacacga caaaggccgc ttgtagcctt ccatccgtga  12600
cctcaatgcg ctgcttaacc agctccacca ggtcggcggt ggcccatatg tcgtaagggc  12660
ttggctgcac cggaatcagc acgaagtcgg ctgccttgat cgcggacaca gccaagtccg  12720
ccgcctgggg cgctccgtcg atcactacga agtcgcgccg gccgatggcc ttcacgtcgc  12780
ggtcaatcgt cgggcggtcg atgccgacaa cggttagcgg ttgatcttcc cgcacggccg  12840
cccaatcgcg ggcactgccc tggggatcgg aatcgactaa cagaacatcg gccccggcga  12900
gttgcagggc gcgggctaga tgggttgcga tggtcgtctt gcctgacccg cctttctggt  12960
taagtacagc gataaccttc atgcgttccc cttgcgtatt tgtttattta ctcatcgcat  13020
catatacgca gcgaccgcat gacgcaagct gttttactca aatacacatc acctttttag  13080
acggcggcgc tcggtttctt cagcggccaa gctggccggc caggccgcca gcttggcatc  13140
agacaaaccg gccaggattt catgcagccg cacggttgag acgtgcgcgg gcggctcgaa  13200
cacgtacccg gccgcgatca tctccgcctc gatctcttcg gtaatgaaaa acggttcgtc  13260
ctggccgtcc tggtgcggtt tcatgcttgt tcctcttggc gttcattctc ggcggccgcc  13320
agggcgtcgg cctcggtcaa tgcgtcctca cggaaggcac cgcgccgcct ggcctcggtg  13380
ggcgtcactt cctcgctgcg ctcaagtgcg cggtacaggg tcgagcgatg cacgccaagc  13440
agtgcagccg cctctttcac ggtgcggcct tcctggtcga tcagctcgcg ggcgtgcgcg  13500
atctgtgccg gggtgagggt agggcggggg ccaaacttca cgcctcgggc cttggcggcc  13560
tcgcgcccgc tccgggtgcg gtcgatgatt agggaacgct cgaactcggc aatgccggcg  13620
aacacggtca acaccatgcg gccggccggc gtggtggtaa cgcgtg                 13666
```

<210> SEQ ID NO 10
<211> LENGTH: 26
<212> TYPE: DNA
<213> ORGANISM: Artificial sequence
<220> FEATURE:
<223> OTHER INFORMATION: primer

<400> SEQUENCE: 10

```
ccggtaccat ggcttcgttc atagat                                          26
```

<210> SEQ ID NO 11
<211> LENGTH: 26
<212> TYPE: DNA
<213> ORGANISM: Artificial sequence
<220> FEATURE:
<223> OTHER INFORMATION: primer

<400> SEQUENCE: 11

```
ttgtcgacct aatcgtcaag ccaatc                                          26
```

UNITED STATES PATENT AND TRADEMARK OFFICE
CERTIFICATE OF CORRECTION

PATENT NO. : 10,696,980 B2
APPLICATION NO. : 15/681684
DATED : June 30, 2020
INVENTOR(S) : Holger Schultheiss It is certified that error appears in the above-identified patent and that said Letters Patent is hereby corrected as shown below:

In the Claims

At Column 53, Line 11, "*Phakopsora paryhizi*" should be -- *Phakopsora pachyrhizi* --.

Signed and Sealed this
Twenty-third Day of April, 2024

Katherine Kelly Vidal
*Director of the United States Patent and Trademark Office*